(12) United States Patent
Kurihara et al.

(10) Patent No.: US 10,435,728 B2
(45) Date of Patent: Oct. 8, 2019

(54) ENDOXYLANASE MUTANT, ENZYME COMPOSITION FOR BIOMASS DECOMPOSITION, AND METHOD OF PRODUCING SUGAR SOLUTION

(71) Applicants: Toray Industries, Inc., Tokyo (JP); National Institute of Advanced Industrial Science and Technology, Tokyo (JP)

(72) Inventors: Hiroyuki Kurihara, Kanagawa (JP); Takuya Kasahara, Kanagawa (JP); Chiaki Yamada, Kanagawa (JP); Natsuko Murakami, Kanagawa (JP); Katsushige Yamada, Kanagawa (JP); Kazuhiko Ishikawa, Hiroshima (JP); Masahiro Watanabe, Hiroshima (JP)

(73) Assignees: Toray Industries, Inc., Tokyo (JP); National Institute of Advanced Industrial Science and Technology, Tokyo (JP)

( * ) Notice: Subject to any disclaimer, the term of this patent is extended or adjusted under 35 U.S.C. 154(b) by 92 days.

(21) Appl. No.: 15/521,654

(22) PCT Filed: Nov. 5, 2015

(86) PCT No.: PCT/JP2015/081151
§ 371 (c)(1),
(2) Date: Apr. 25, 2017

(87) PCT Pub. No.: WO2016/072448
PCT Pub. Date: May 12, 2016

(65) Prior Publication Data
US 2017/0240941 A1    Aug. 24, 2017

(30) Foreign Application Priority Data

Nov. 5, 2014 (JP) .................... 2014-225543

(51) Int. Cl.
| C12P 19/14 | (2006.01) |
| C12N 5/00 | (2006.01) |
| C12N 15/09 | (2006.01) |
| C12N 9/24 | (2006.01) |
| C12P 19/02 | (2006.01) |

(52) U.S. Cl.
CPC ............ *C12P 19/14* (2013.01); *C12N 5/00* (2013.01); *C12N 9/2482* (2013.01); *C12N 15/09* (2013.01); *C12P 19/02* (2013.01); *C12Y 302/01008* (2013.01)

(58) Field of Classification Search
None
See application file for complete search history.

(56) References Cited

U.S. PATENT DOCUMENTS

| 8,623,629 | B2 * | 1/2014 | Sibbesen ................ C12N 9/248 435/200 |
| 8,951,751 | B2 * | 2/2015 | Sibbesen .......... C12Y 302/0100 435/18 |
| 9,663,776 | B2 * | 5/2017 | Ishikawa ................ C12N 9/248 |
| 2003/0108642 | A1 | 6/2003 | Sabatier et al. |
| 2008/0171374 | A1 | 7/2008 | Fenel et al. |
| 2012/0094320 | A1 | 4/2012 | Yoshioka et al. |
| 2015/0044728 | A1 | 2/2015 | Fukuura et al. |

FOREIGN PATENT DOCUMENTS

| CN | 103642777 | 3/2014 |
| JP | 2002-513595 A | 5/2002 |
| JP | 2002-199890 A | 7/2002 |
| JP | 2003-511066 A | 3/2003 |
| JP | 2006-271379 A | 10/2006 |
| JP | 2013-243954 A | 12/2013 |
| JP | 2014-64563 A | 4/2014 |
| WO | 01/27252 A1 | 4/2001 |
| WO | 2009/154247 A1 | 12/2009 |
| WO | 2013/103127 A1 | 7/2013 |

OTHER PUBLICATIONS

Coughlan, M. P. et al., "β-1,4-$_D$-Xylan-degrading enzyme systems: biochemistry, molecular biology and applications", *Biotechnol. Appl. Biochem.*, 1993, 17, pp. 259-289.
Coutinho, P. M. et al., "Carbohydrate-Active Enzymes: An Integrated Database Approach", *Recent Advances in Carbohydrate Bioengineering*, 1999, 246, pp. 3-12.
Beaugrand, J. et al , "Impact and efficiency of GH10 and GH11 thermostable endoxylanases on wheat bran and alkali-extractable arabinoxylans", *Carbohydr. Res.*, 2004, 339, pp. 2529-2540.
Fujii, T. et al., "Enzymatic hydrolyzing performance of *Acremonium cellulolyticus* and *Trichoderma reesei* against three lignocellulosic materials", *Biotechnol. Biofuels.*, 2009, 2, 24.
Gruber, K. et al., "Thermophilic Xylanase from *Thermomyces lanuginosus*: High-Resolution X-ray Structure and Modeling Studies", *Biochemistry*, 1998, vol. 37, No. 39, pp. 13475-13485.
Supplementary European Search Report dated Apr. 6, 2018, of corresponding European Application No. 15856688.5.
Kataoka, M., et al., "Crystal Structure of *Talaromyces cellulolyticus* (Formerly Known as *Acremonium cellulolyticus*) GH Family 11 Xylanase," *Applied Biochemistry and Biotechnology*, vol. 174, No. 4, Aug. 20, 2014, pp. 1599-1612.
Verma, D., et al, "Molecular approaches for ameliorating microbial xylanases," *Bioresource Technology*, vol. 117, Apr. 11, 2012, pp. 360-367.

* cited by examiner

Primary Examiner — Hope A Robinson
(74) Attorney, Agent, or Firm — DLA Piper LLP (US)

(57) ABSTRACT

An endoxylanase mutant has improved thermal stability. The endoxylanase mutant having endoxylanase activity includes an amino acid sequence at least including substitution of an amino acid residue at one or more positions selected from positions corresponding to position 35, position 44, position 62, position 63, position 101, and position 102 of an amino acid sequence of SEQ ID NO: 1 in an amino acid sequence of endoxylanase derived from a filamentous fungus.

16 Claims, 1 Drawing Sheet

Specification includes a Sequence Listing.

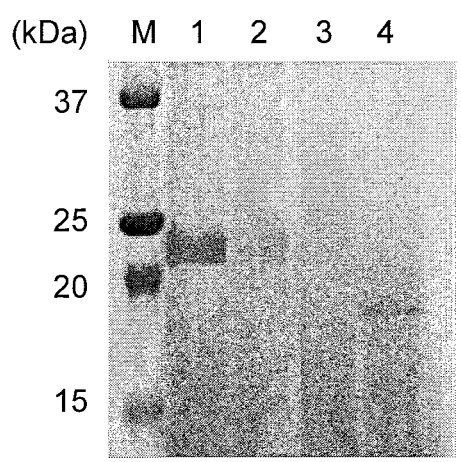

ENDOXYLANASE MUTANT, ENZYME COMPOSITION FOR BIOMASS DECOMPOSITION, AND METHOD OF PRODUCING SUGAR SOLUTION

TECHNICAL FIELD

This disclosure relates to a novel endoxylanase mutant, an enzyme composition for biomass decomposition containing the same, and a method of producing a sugar solution.

BACKGROUND

Among various methods of saccharification of cellulose, enzymatic saccharification methods, which require small energy usage and provide high sugar yield, are considered as the mainstream of development. Cellulose is contained in a large amount in herbaceous plants and woody plants, and such plants are collectively referred to as cellulose-containing biomass. Cellulose-containing biomass contains hemicellulose such as xylan and arabinan and lignin in addition to cellulose. Xylan has a β-1,4-linked D-xylose backbone, and the backbone may be partially modified with O-acetyl, β-arabinofuranosyl, glucuronic acid, or a phenolic acid (Coughlan, M. P. et al., Biotechnol. Appl. Biochem. 17, 259-289 (1993)). Xylanase, which acts on the β-1,4-linked xylose backbone, is one of important enzymes to decompose cellulose-containing biomass.

Xylanases are classified into family 10 (GH10) and family 11 (GH11) on the basis of the homology of the amino acid sequence (Coutinho, P. M. et al., Recent Advances in Carbohydrate Bioengineering, 246, 3-12 (1999)). Xylanases belonging to GH10 generally have a molecular weight of 30 kDa or higher and, in contrast, xylanases belonging to GH11 are generally considered as having a relatively small molecular weight of approximately 20 kDa (Beaugrand et al., Carbohydr. Res. 339, 2529-2540 (2004)).

Filamentous fungi are known to be microorganisms to decompose a wide variety of cellulosic biomasses. Cellulase produced by *Acremonium cellulolyticus* in a culture solution is known to provide a higher glucose yield than cellulase produced by *Trichoderma reesei* in the decomposition of cellulose-containing biomass (Fujii et al., Biotechnol. Biofuels. 2, 24 (2009)). In recent years, seven types of xylanases have been cloned from *Acremonium cellulolyticus*, and the functions of the wild-type enzymes have been analyzed (Watanabe et al., AMB Express. 4, 27). Watanabe et al. report that XylC has the highest xylanolytic activity among the seven types of xylanases, although the expression level is the lowest in *Acremonium cellulolyticus*.

It could therefore be helpful to provide a novel endoxylanase mutant having improved thermal stability. In addition, it could be helpful to provide an exogenous enzyme containing the same, and an efficient method of producing a sugar solution.

The Applicants hereby incorporate by reference the sequence listing contained in the ASCII text file titled SequenceListing.txt, created Apr. 19, 2017 and having 44.9 KB of data.

SUMMARY

We found that substitution of an amino acid residue with another amino acid residue at one or two or more positions selected from positions corresponding to position 35, position 44, position 62, position 63, position 101, and position 102 of an amino acid sequence of SEQ ID NO: 1 in an amino acid sequence of endoxylanase derived from a filamentous fungus, may improve the thermal stability of the endoxylanase. We thus provide:

[1] An endoxylanase mutant having endoxylanase activity and comprising an amino acid sequence at least including substitution of an amino acid residue at one or more positions selected from positions corresponding to position 35, position 44, position 62, position 63, position 101, and position 102 of an amino acid sequence of SEQ ID NO: 1 in an amino acid sequence of endoxylanase derived from a filamentous fungus.

[2] The endoxylanase mutant according to [1], wherein an amino acid residue at positions or a position corresponding to position 35 and/or position 62 of an amino acid sequence of SEQ ID NO: 1 is substituted with cysteine.

[3] The endoxylanase mutant according to [1] or [2], wherein an amino acid residue at positions or a position corresponding to position 44 and/or position 63 of an amino acid sequence of SEQ ID NO: 1 is substituted with an amino acid independently, for each position, selected from, or selected from histidine, glycine, tryptophan, methionine, proline, alanine, phenylalanine, valine, leucine, and isoleucine.

[4] The endoxylanase mutant according to any of [1] to [3], wherein an amino acid residue at positions or a position corresponding to position 101 and/or position 102 of an amino acid sequence of SEQ ID NO: 1 is substituted with an amino acid independently, for each position, selected from, or selected from proline and asparagine.

[5] The endoxylanase mutant according to any of [1] to [4], wherein an amino acid residue at one or more positions selected from positions corresponding to position 61, position 65, and position 66 of an amino acid sequence of SEQ ID NO: 1 is further substituted.

[6] The endoxylanase mutant according to any of [1] to [5], wherein an amino acid residue at all of positions corresponding to position 35, position 44, position 61, position 62, position 63, position 65, position 66, position 101, and position 102 of an amino acid sequence of SEQ ID NO: 1 is substituted.

[7] The endoxylanase mutant according to any of [1] to [6], wherein the endoxylanase derived from a filamentous fungus is derived from *Acremonium cellulolyticus*.

[8] The endoxylanase mutant according to any of [1] to [7], having endoxylanase activity and consisting of any of:
   (a) an amino acid sequence as set forth in SEQ ID NO: 3, 4, 5, 6, 7, 8, 9, 10, or 45;
   (b) an amino acid sequence including deletion, substitution, or addition of an amino acid at one to several positions without mutating a substituted amino acid or substituted amino acids at position 35, position 44, position 61, position 62, position 63, position 65, position 66, position 101, and position 102 in the amino acid sequence as set forth in SEQ ID NO: 3, 4, 5, 6, 7, 8, 9, 10, or 45; and
   (c) an amino acid sequence having 90% or more of sequence identity to an amino acid sequence as set forth in SEQ ID NO: 3, 4, 5, 6, 7, 8, 9, 10, or 45 excluding a substituted amino acid or substituted amino acids at position 35, position 44, position 61, position 62, position 63, position 65, position 66, position 101, and position 102 without mutating the substituted amino acid or substituted amino acids.

[9] A DNA encoding the endoxylanase mutant according to any of [1] to [8].

[10] An expression vector comprising the DNA according to [9].

[11] A transformed cell prepared through transformation by using the expression vector according to [10].
[12] A method of producing an endoxylanase mutant, the method comprising a step of culturing the transformed cell according to [11] to obtain an endoxylanase mutant produced by the transformed cell.
[13] An enzyme composition for biomass decomposition, the enzyme composition comprising the endoxylanase mutant according to any of [1] to [8].
[14] The enzyme composition for biomass decomposition according to [13], the enzyme composition further comprising one or two or more enzymes selected from the group consisting of cellobiohydrolase, endoglucanase, β-glucosidase, β-xylosidase, mannanase, mannosidase, glucoamylase, α-amylase, esterase, and lipase.
[15] A method of producing a sugar solution from biomass, the method comprising adding the enzyme composition for biomass decomposition according to [13] or [14] to the biomass.

We provide an endoxylanase mutant having improved thermal stability. In particular, the endoxylanase mutant has advantages of having improved thermal stability under a high temperature condition, specifically at 65° C. or higher, and having enhanced xylanolytic activity. Accordingly, the endoxylanase mutant and an enzyme composition containing the endoxylanase mutant can be suitably used for production of a sugar solution from cellulose-containing biomass.

BRIEF DESCRIPTION OF THE DRAWING

FIG. 1 is a photographic image showing the result of SDS-PAGE for culture supernatants of the yeast *Pichia pastoris* expressing wild-type endoxylanase or an endoxylanase mutant. M: marker; 1: culture supernatant containing wild-type endoxylanase; 2: culture supernatant containing endoxylanase mutant including substitution at position 35 and position 62; 3: culture supernatant containing endoxylanase mutant including substitution at position 35, position 44, position 62, position 61, position 65, position 63, and position 66; 4: culture supernatant containing endoxylanase mutant including substitution at position 35, position 44, position 62, position 101, position 102, position 61, position 65, position 63, and position 66.

DETAILED DESCRIPTION

Our enzymes, compositions and methods will be described in detail in the following, but this disclosure is not limited thereto.
(1) Endoxylanase Mutant
"Endoxylanase" is an enzyme having activity to hydrolyze hemicellulose by acting on the β-1,4-linked xylose backbone (endoxylanase activity) and classified as EC 3.3.1.8. Endoxylanases are classified into two types, i.e., family 10 (GH10) and family 11 (GH11), and the endoxylanase is an enzyme belonging to family 11 (GH11) and has a β-jelly roll structure. Measurement of "endoxylanase activity" can be performed by using β-1,4-linked D-xyloses for the substrate, preferably by using Birchwood xylan sold as a reagent for the substrate. The presence or absence of decomposition of xylan as the substrate can be determined through measurement of the quantity of a reducing sugar contained in the reaction solution after the reaction. The quantity of a reducing sugar can be measured by using a dinitrosalicylic acid method (DNS method), and a method described in Bailey et al., "Interlaboratory testing of methods for assay of xylanase activity", J. Biotechnol. 23, 257-270, can be preferably used. Conditions for activity measurement are not particularly limited as long as the activity of endoxylanase can be measured by the above method. A preferred temperature condition for activity measurement is 20° C. to 90° C., preferably 40° C. to 75° C., and the pH is preferably 4 to 9, further preferably pH 5 to 7, and the reaction time is preferably 1 second to 600 minutes, most preferably 1 minute to 60 minutes. The content of xylan to be used for the substrate in activity measurement is preferably 0.1% by weight to 10% by weight, most preferably 0.5% by weight to 2% by weight.

Endoxylanase derived from a filamentous fungus can be used, examples of which include *Trichoderma, Aspergillus, Cellulomonas, Clostridium, Streptomyces, Humicola, Acremonium, Irpex, Mucor,* and *Talaromyces*, and endoxylanase derived from *Acremonium* can be preferably used. For the endoxylanase, endoxylanase isolated from *Acremonium cellulolyticus* can be particularly preferably used. Endoxylanases derived from *Acremonium cellulolyticus* are known, and registered, for example, as AB874990, AB874991, AB874992, AB874993, AB874994, AB874995, AB874995, and AB874996 in GenBank, and the gene information or the like can be used.

Endoxylanase preferably comprises or consists of the amino acid sequence as set forth in SEQ ID NO: 1.

Endoxylanase encompasses a part of the endoxylanase which retains endoxylanase activity. "A part of endoxylanase" consists of a fragment of endoxylanase obtained by removing any partial region thereof, the fragment of endoxylanase retaining at least 40% or more, 50% or more, 60% or more, 70% or more, 80% or more, 90% or more, 95% or more, or 99% or more of the original endoxylanase activity, and examples of such fragments include a fragment of endoxylanase obtained by removing a signal peptide region from the endoxylanase. Examples of the signal peptide include a region represented by the amino acid sequence from position 1 to position 34 in the amino acid sequence as set forth in SEQ ID NO: 1. A part of endoxylanase preferably comprises or consists of the amino acid sequence as set forth in SEQ ID NO: 2.

The "endoxylanase mutant" refers to a protein having endoxylanase activity and including an amino acid sequence including substitution of an amino acid residue with another amino acid at one or two or more positions selected from positions corresponding to position 35, position 44, position 62, position 63, position 101, and position 102 of the amino acid sequence of SEQ ID NO: 1 in the amino acid sequence of the above "endoxylanase". More preferably, the endoxylanase mutant includes substitution of an amino acid at two, three, four, five, or six positions selected from positions corresponding to position 35, position 44, position 62, position 63, position 101, and position 102 of the amino acid sequence of SEQ ID NO: 1. Particularly preferably, the endoxylanase mutant includes substitution of an amino acid at all of the six positions corresponding to position 35, position 44, position 62, position 63, position 101, and position 102 of the amino acid sequence of SEQ ID NO: 1.

The "endoxylanase mutant" includes substitution of an amino acid at the above position or positions, and as a consequence has higher thermal resistance than endoxylanase that does not include such substitution of an amino acid.

The positions of an amino acid specified by "positions corresponding to position 35, position 44, position 62, position 63, position 101, and position 102 of the amino acid sequence of SEQ ID NO: 1" in the amino acid sequence of the above endoxylanase can be determined by using a method including the following steps 1) to 3).

Step 1) The initial methionine of the amino acid sequence of SEQ ID NO: 1 is defined as position 1. Following positions of the amino acid sequence are sequentially numbered to define positions 2, 3, 4 and so on.

Step 2) Subsequently determined are the positions of an amino acid corresponding to position 35, position 44, position 62, position 63, position 101, and position 102 of the amino acid sequence as set forth in SEQ ID NO: 1 in the amino acid sequence of the above endoxylanase. The corresponding positions of an amino acid can be identified by aligning the amino acid sequence of the above endoxylanase with the amino acid sequence of SEQ ID NO: 1. This operation is called alignment of an amino acid sequence. Many, well-known types of software such as ClustalW can be used for an alignment tool with default parameters. Through alignment between amino acid sequences different in length, those skilled in the art can identify the positions of an amino acid corresponding to position 35, position 44, position 62, position 63, position 101, and position 102 of the amino acid sequence as set forth in SEQ ID NO: 1 in the amino acid sequence of the above endoxylanase.

Step 3) Positions identified in the alignment analysis as positions corresponding to position 35, position 44, position 62, position 63, position 101, and position 102 of the amino acid sequence of SEQ ID NO: 1 are defined as "positions corresponding to position 35, position 44, position 62, position 63, position 101, and position 102 of the amino acid sequence of SEQ ID NO: 1" in the amino acid sequence of the "endoxylanase".

If the endoxylanase includes mutation such as deletion, substitution, addition, and insertion of an amino acid at a position other than the "positions corresponding to position 35, position 44, position 62, position 63, position 101, and position 102 of the amino acid sequence of SEQ ID NO: 1", or if the endoxylanase is a part of endoxylanase as described above, the "positions corresponding to position 35, position 44, position 62, position 63, position 101, and position 102 of the amino acid sequence of SEQ ID NO: 1" may be different from the 35th position, 44th position, 62nd position, 63rd position, 101st position, and 102nd position, respectively, from the N-terminal. Also in such cases, positions determined by using the above method are defined as "positions corresponding to position 35, position 44, position 62, position 63, position 101, and position 102 of the amino acid sequence of SEQ ID NO: 1".

Substitution of an amino acid at each position is not particularly limited and only required to be substitution with another amino acid. However, the following types of substitution with an amino acid are preferably included:
position 35: cysteine;
position 44: histidine, glycine, tryptophan, methionine, proline, alanine, phenylalanine, valine, leucine, or isoleucine, preferably histidine;
position 62: cysteine;
position 63: histidine, glycine, tryptophan, methionine, proline, alanine, phenylalanine, valine, leucine, or isoleucine, preferably leucine;
position 101: proline or asparagine, preferably proline; and
position 102: proline or asparagine, preferably asparagine.

Substitution of an amino acid with cysteine at both of the positions corresponding to position 35 and position 62 is preferred because a disulfide linkage can be formed between the cysteine side chains at the positions.

When the endoxylanase mutant is expressed in a eukaryote as a host, each amino acid at positions corresponding to position 101 and position 102 may remain the unsubstituted, wild-type amino acid. Positions corresponding to position 101 and position 102 may be included in an amino acid sequence to be glycosylated in a eukaryote.

The "endoxylanase mutant" may include substitution of an amino acid at one or two or more positions selected from positions corresponding to position 61, position 65, and position 66 of the amino acid sequence of SEQ ID NO: 1, in addition to substitution of an amino acid at a position or positions selected from positions corresponding to position 35, position 44, position 62, position 63, position 101, and position 102 of the amino acid sequence of SEQ ID NO: 1. Substitution of an amino acid further included at these positions can provide higher thermal resistance. Preferably, the endoxylanase mutant further includes substitution of an amino acid at two or three positions selected from positions corresponding to position 61, position 65, and position 66 of the amino acid sequence of SEQ ID NO: 1. More preferably, the endoxylanase mutant further includes substitution of an amino acid at three positions corresponding to position 61, position 65, and position 66 of the amino acid sequence of SEQ ID NO: 1.

Substitution of an amino acid at each position is not particularly limited and only required to be substitution with another amino acid. However, the following types of substitution with an amino acid are included:
position 61: glycine, tryptophan, methionine, proline, alanine, phenylalanine, valine, leucine, or isoleucine, preferably methionine;
position 65: proline; and
position 66: glycine, tryptophan, methionine, proline, alanine, phenylalanine, valine, leucine, or isoleucine, preferably glycine.

In one example, the endoxylanase mutant comprises or consists of a polypeptide having endoxylanase activity and including an amino acid sequence or a part thereof, the amino acid sequence being the amino acid sequence of SEQ ID NO: 1 including substitution of an amino acid at one or two or more positions selected from position 35, position 44, position 62, position 63, position 101, and position 102. Examples of "a part thereof" include polypeptides obtained by removing the signal peptide region. More specific examples of such endoxylanase mutants include:

an endoxylanase mutant including substitution with cysteine at position 35, the endoxylanase mutant comprising or consisting of the amino acid sequence of SEQ ID NO: 3 (the amino acid sequence of SEQ ID NO: 3 does not include the above signal peptide region);

an endoxylanase mutant including substitution with cysteine at position 62, the endoxylanase mutant comprising or consisting of the amino acid sequence of SEQ ID NO: 5 (the above amino acid sequence of SEQ ID NO: 5 does not include the signal peptide region);

an endoxylanase mutant including substitution with cysteine at both of position 35 and position 62, the endoxylanase mutant comprising or consisting of the amino acid sequence of SEQ ID NO: 9 (the amino acid sequence of SEQ ID NO: 9 does not include the above signal peptide region);

an endoxylanase mutant including substitution with histidine at position 44, the endoxylanase mutant comprising or consisting of the amino acid sequence of SEQ ID NO: 4 (the amino acid sequence of SEQ ID NO: 4 does not include the above signal peptide region);

an endoxylanase mutant including substitution with leucine at position 63, the endoxylanase mutant comprising or consisting of the amino acid sequence of SEQ ID NO: 6 (the amino acid sequence of SEQ ID NO: 6 does not include the above signal peptide region);

an endoxylanase mutant including substitution with proline at position 101, the endoxylanase mutant comprising the amino acid of SEQ ID NO: 7 or consisting of the amino acid sequence of SEQ ID NO: 7 (the amino acid sequence of SEQ ID NO: 7 does not include the above signal peptide region); and an endoxylanase mutant including substitution with asparagine at position 102, the endoxylanase mutant comprising the amino acid of SEQ ID NO: 8 or consisting of the amino acid sequence of SEQ ID NO: 8 (the amino acid sequence of SEQ ID NO: 8 does not include the above signal peptide region).

Particularly preferably, the endoxylanase mutant is an endoxylanase mutant including all of the above six types of substitution at position 35, position 44, position 62, position 63, position 101, and position 102, or a part of the endoxylanase mutant.

In another example, the endoxylanase mutant comprises or consists of a polypeptide having endoxylanase activity and including an amino acid sequence or a part thereof, the amino acid sequence being the amino acid sequence of SEQ ID NO: 1 including substitution of an amino acid at one or two or more positions selected from position 61, position 65, and position 66 in addition to substitution of an amino acid at a position or positions selected from position 35, position 44, position 62, position 63, position 101, and position 102.

In still another example, the endoxylanase mutant comprises or consists of a polypeptide having endoxylanase activity and including an amino acid sequence or a part thereof, the amino acid sequence being the amino acid sequence of SEQ ID NO: 1 including substitution of an amino acid at seven positions of position 35, position 44, position 62, position 63, position 61, position 65, and position 66. More specifically, such an endoxylanase mutant comprises the amino acid of SEQ ID NO: 45 or consists of the amino acid sequence of SEQ ID NO: 45 (the amino acid sequence of SEQ ID NO: 45 does not include the above signal peptide region).

In yet another example, the endoxylanase mutant comprises or consists of a polypeptide having endoxylanase activity and including an amino acid sequence or a part thereof, the amino acid sequence being the amino acid sequence of SEQ ID NO: 1 including substitution of an amino acid at nine positions of position 35, position 44, position 62, position 63, position 101, position 102, position 61, position 65, and position 66. More specifically, such an endoxylanase mutant comprises the amino acid of SEQ ID NO: 10 or consists of the amino acid sequence of SEQ ID NO: 10 (the amino acid sequence of SEQ ID NO: 10 does not include the above signal peptide region).

The endoxylanase mutant encompasses a protein having endoxylanase activity and including the amino acid sequence of the endoxylanase mutant or a part thereof, the amino acid sequence including deletion, substitution, addition, or insertion of an amino acid at one or several positions without mutating the substituted amino acid or substituted amino acids at position 35, position 44, position 61, position 62, position 63, position 65, position 66, position 101, and position 102. The range of "one or several" is not particularly limited and, for example, is 10 or less, further preferably 5 or less, and particularly preferably 4 or less, or one or two.

The endoxylanase mutant also encompasses a protein having endoxylanase activity and comprising, preferably consisting of, an amino acid sequence having 90%, 95%, 99%, or more of identity to the amino acid sequence of the endoxylanase mutant or a part thereof, the amino acid sequence excluding the substituted amino acid or substituted amino acids at position 35, position 44, position 61, position 62, position 63, position 65, position 66, position 101, and position 102 without mutating the substituted amino acid or substituted amino acids, as calculated by using a BLAST (Basic Local Alignment Search Tool at the National Center for Biological Information) or the like (e.g., using default or initial parameters). "Identity" refers to the fraction (percentage) of identical amino acid residues and similar amino acid residues to the total of overlapping amino acid residues in an optimum alignment when two amino acid sequences are aligned with or without introduction of a gap. Identity can be determined by using a method well-known to those skilled in the art or software for alignment analysis (e.g., a known algorism such as BLAST and FASTA) or the like.

An additional peptide or protein may be added to the N-terminal and/or C-terminal of the endoxylanase mutant. Examples of such peptides or proteins include methionine as a translation start site, a secretion signal sequence, a transport protein, a binding protein, a tag peptide for purification, a heterologous hydrolase, and a fluorescent protein. Those skilled in the art can select a peptide or protein having a function to impart from the above peptides or proteins in accordance with the purpose and add the selected peptide or protein to the endoxylanase mutant.

(2) Method of Producing Endoxylanase Mutant

The endoxylanase mutant can be produced, for example, by preparing a DNA encoding the amino acid sequence of the endoxylanase mutant as described in (1), linking the DNA to an expression vector, introducing the expression vector into a host to produce the endoxylanase mutant as a heterologous or homologous protein, and isolating and purifying the endoxylanase mutant. The frequency of codon usage to encode the amino acid sequence may be identical to that of a filamentous fungus from which the endoxylanase is derived such as *Acremonium cellulolyticus*, or may be changed in accordance with the frequency of codon usage of a host.

A conventionally known method can be used to prepare a DNA encoding the above-described endoxylanase mutant, and examples of such methods include a method of performing total synthesis of a DNA encoding an intended amino acid sequence by using gene synthesis, and a method of introducing mutation into a DNA encoding endoxylanase or a part thereof isolated from a filamentous fungus by using site-specific mutagenesis to allow the DNA encoding an amino acid at a position specified in the above to encode another amino acid specified in the above. Site-specific mutagenesis to mutate at an intended site of a DNA can be performed by using the conventional, common PCR method.

For the DNA encoding the endoxylanase, a DNA encoding endoxylanase isolated from *Acremonium cellulolyticus* can be particularly preferably used. For example, a DNA comprising or consisting of the nucleotide sequence as set forth in SEQ ID NO: 32, or a DNA comprising or consisting of the nucleotide sequence as set forth in SEQ ID NO: 33, which is obtained by removing a region encoding a signal peptide from the nucleotide sequence as set forth in SEQ ID NO: 32, can be used for the DNA encoding the endoxylanase. These DNAs can be obtained by isolating a DNA from *Acremonium cellulolyticus* in accordance with a known method and amplifying the DNA by using PCR or the like.

In one example, the DNA encoding the endoxylanase mutant comprises or consists of a DNA encoding a polypeptide having endoxylanase activity and including an amino acid sequence or a part thereof, the amino acid sequence including substitution of an amino acid at one or two or more positions selected from position 35, position 44, position 62, position 63, position 101, and position 102 of the amino acid sequence of SEQ ID NO: 1. More specific examples of such a DNA encoding the endoxylanase mutant include:

a DNA encoding an endoxylanase mutant including substitution with cysteine at position 35, the DNA comprising or consisting of the nucleotide sequence of SEQ ID NO: 34 (the DNA does not encode the above signal peptide region);

a DNA encoding an endoxylanase mutant including substitution with cysteine at position 62, the DNA comprising or consisting of the nucleotide sequence of SEQ ID NO: 36 (the DNA does not encode the above signal peptide region);

a DNA encoding an endoxylanase mutant including substitution with cysteine at both of position 35 and position 62, the DNA comprising or consisting of the nucleotide sequence of SEQ ID NO: 40 (the DNA does not encode the above signal peptide region);

a DNA encoding an endoxylanase mutant including substitution with histidine at position 44, the DNA comprising or consisting of the nucleotide sequence of SEQ ID NO: 35 (the DNA does not encode the above signal peptide region);

a DNA encoding an endoxylanase mutant including substitution with leucine at position 63, the DNA comprising or consisting of the nucleotide sequence of SEQ ID NO: 37 (the DNA does not encode the above signal peptide region);

a DNA encoding an endoxylanase mutant including substitution with proline at position 101, the DNA comprising or consisting of the nucleotide sequence of SEQ ID NO: 38 (the DNA does not encode the above signal peptide region); and a DNA encoding an endoxylanase mutant including substitution with asparagine at position 102, the DNA comprising or consisting of the nucleotide sequence of SEQ ID NO: 39 (the DNA does not encode the above signal peptide region).

In still another example, the DNA encoding the endoxylanase mutant comprises or consists of a DNA encoding a polypeptide having endoxylanase activity and including an amino acid sequence or a part thereof, the amino acid sequence being the amino acid sequence of SEQ ID NO: 1 including substitution at three positions, specifically, substitution with methionine at position 61, substitution with aspartic acid at position 65, and substitution with asparagine at position 66 in addition to the above-described substitution at four positions of position 35, position 44, position 62, and position 63. The DNA encoding the endoxylanase mutant comprises or consists of the nucleotide sequence of SEQ ID NO: 49 (the DNA does not encode the above signal peptide region).

In still another example, the DNA encoding the endoxylanase mutant comprises or consists of a DNA encoding a polypeptide having endoxylanase activity and including an amino acid sequence or a part thereof, the amino acid sequence being the amino acid sequence of SEQ ID NO: 1 including substitution at three positions, specifically, substitution with methionine at position 61, substitution with aspartic acid at position 65, and substitution with asparagine at position 66 in addition to the above-described substitution at six positions of position 35, position 44, position 62, position 63, position 101, and position 102. The DNA encoding the endoxylanase mutant comprises or consists of the nucleotide sequence of SEQ ID NO: 41 (the DNA does not encode the above signal peptide region).

The DNA encoding the endoxylanase mutant encompasses any DNA which does not mutate the substituted amino acid or substituted amino acids at position 35, position 44, position 61, position 62, position 63, position 65, position 66, position 101, and position 102, and encodes a polypeptide having endoxylanase activity, and such a DNA comprises or consists of:

a nucleotide sequence including deletion, substitution, addition, or insertion of a nucleotide at one to several positions in one of the above nucleotide sequences, for example, a nucleotide sequence including deletion, substitution, addition, or insertion of a nucleotide at 1 to 100 positions, preferably at 1 to 50 positions, more preferably at 1 to 10 positions in the nucleotide sequence as set forth in SEQ ID NO: 1;

a nucleotide sequence having sequence identity of 80% or more, more preferably 90% or more, further preferably 95% or more, most preferably 99% or more to one of the above nucleotide sequences, where comparison of nucleotide sequences can be performed by using a known method, for example, by using a BLAST or the like with a default setting; or a nucleotide sequence hybridizable with a DNA consisting of a sequence complementary to one of the above nucleotide sequences under stringent conditions, where "stringent conditions" refer to such conditions that a specific hybrid is formed and a non-specific hybrid is not formed, for example, conditions such that hybridization is performed in a solution containing 2 to 6×SSC (composition of 1×SSC: 0.15 M NaCl, 0.015 M sodium citrate, pH 7.0) and 0.1 to 0.5% SDS at 42 to 55° C. and washing is performed in a solution containing 0.1 to 0.2×SSC and 0.1 to 0.5% SDS at 55 to 65° C.

The DNA encoding the endoxylanase mutant prepared as described above is linked to the downstream of a promoter in a suitable expression vector by using a restriction enzyme and DNA ligase, and thus an expression vector including the DNA can be produced.

Examples of expression vectors include bacterial plasmids, yeast plasmids, phage DNAs (e.g., the lambda phage), virus DNAs of retroviruses, baculoviruses, vaccinia viruses, adenoviruses and the like, SV40 derivatives, and *Agrobacterium* as a vector for plant cells, and any other vector capable of replicating and surviving in a host cell can be used. When the host is *Escherichia coli*, examples of the expression vector may include the pUC, pET, and pBAD. When the host is yeast, examples of the expression vector include the pPink-HC, pPink-LC, pPinka-HC, pPCIZ, pPCIZa, pPCI6, pPCI6α, pFLD1, pFLD1α, pGAPZ, pGAPZα, pPIC9K, pPIC9, pD912, and pD915.

The promoter may be any promoter adapted to and suitable for a host used for gene expression. When the host is *Escherichia coli*, examples of the promoter include the lac promoter, Trp promoter, PL promoter, and PR promoter. When the host is yeast, examples of the promoter include the AOX1 promoter, TEF1 promoter, ADE2 promoter, CYC1 promoter, GAL-L1 promoter, and GAP promoter.

For the host cell, for example, *Escherichia coli*, bacteria cells, yeast cells, fungal cells, insect cells, plant cells, and animal cells are preferred. Examples of yeast cells include *Pichia*, *Saccharomyces*, and *Schizosaccharomyces*. Examples of fungal cells include *Aspergillus* and *Trichoderma*. Examples of insect cells include Sf9. Examples of plant cells include cells of dicotyledons. Examples of animal cells include CHO, HeLa, and HEK293. The host is preferably a eukaryotic microorganism, and further preferably a yeast cell or a fungal cell. Use of a yeast cell or fungal cell as a host may be advantageous in that high enzyme production, secretory production of the enzyme to the outside of cells, and/or enhancement of the thermal resistance of the enzyme are provided.

Transformation or transfection can be performed by using a known method such as a calcium phosphate method and electroporation. The endoxylanase mutant can be obtained through expression under control by a promoter in a host cell transformed or transfected as described above followed by collection of the product. For the expression, a host cell transformed or transfected is proliferated or grown to reach a suitable cell density, and a promoter is then induced by a chemical inducing means such as temperature shift and addition of isopropyl-1-thio-β-D-galactoside (IPTG), and the cells are further cultured for a certain period. Alternatively, a promoter is induced by a sugar contained in a medium, by which cell culture and expression can be simultaneously performed.

When an intended endoxylanase mutant is discharged to the outside of cells, the endoxylanase mutant is purified directly from the medium. When the endoxylanase mutant is present outside of cells, the cells are destroyed by using a physical means such as ultrasonic disruption and mechanical disruption or a chemical means such as a cell lysis solution, and the endoxylanase mutant is then purified. Specifically, the endoxylanase mutant can be partially or completely purified from a medium for recombinant cells by using combination of techniques such as with ammonium sulfate precipitation or ethanol precipitation, acid extraction, anion- or cation-exchange chromatography, reversed-phase high-performance chromatography, affinity chromatography, gel filtration chromatography, and electrophoresis.

(3) Enzyme Composition for Biomass Decomposition Containing Endoxylanase Mutant

The biomass enzyme composition is an enzyme composition at least containing the endoxylanase mutant as an active ingredient for hydrolysis of biomass and is used for applications to decompose biomass. Biomass refers to plant bodies derived from organisms, and examples thereof include herbaceous plants, woody plants, algae, seagrasses, sugar crops, resource crops, and grains. Such biomasses each contain polysaccharides having two or more sugar units, and the polysaccharides can be hydrolyzed with the enzyme composition for biomass decomposition. Cellulose-containing biomass can be particularly preferably used. Cellulose-containing biomass is a biological resource containing a cellulose component, and specifically refers to herbaceous biomass such as bagasse, switchgrass, Napier grass, *Erianthus arundinaceus*, corn stover, rice straw, and straw, woody biomass such as trees and construction waste materials, and in addition biomass derived from the aquatic environment such as algae and seagrasses. These cellulosic biomasses contain lignin, which is an aromatic polymer, in addition to cellulose and hemicellulose (hereinafter, cellulose and hemicellulose are collectively referred to as "cellulose").

Purified endoxylanase mutant or crude endoxylanase mutant may be used for the endoxylanase mutant contained in the enzyme composition for biomass decomposition. The endoxylanase mutant contained in the enzyme composition for biomass decomposition may be immobilized on a solid phase. Examples of the solid phase include, but are not limited to, polyacrylamide gel, polystyrene resin, porous glass, and metal oxides. Immobilization of the endoxylanase mutant on a solid phase advantageously allows continuous and repeated use. In addition, a processed product of cells transformed with the DNA encoding the above endoxylanase mutant can be used as a crude endoxylanase mutant. Examples of the "processed product of cells transformed" include transformed cells immobilized on a solid phase, and dead transformed cells, disrupted transformed cells, and products obtained by immobilizing dead transformed cells or disrupted transformed cells on a solid phase.

The enzyme composition for biomass decomposition may contain an additional enzyme in addition to the endoxylanase mutant. The enzyme composition for biomass decomposition preferably contains a hydrolase involving in biomass decomposition. Examples of such additional enzymes include cellobiohydrolase, endoglucanase, β-glucosidase, β-xylosidase, mannanase, mannosidase, glucoamylase, α-amylase, esterase, and lipase.

The additional enzyme is preferably an enzyme produced by a microorganism such as a filamentous fungus. Examples of filamentous fungi include microorganisms belonging to *Trichoderma*, *Aspergillus*, *Cellulomonas*, *Clostridium*, *Streptomyces*, *Humicola*, *Acremonium*, *Irpex*, *Mucor*, and *Talaromyces*. Since these microorganisms produce an enzyme in a culture solution, the culture solution may be directly used as an unpurified enzyme in combination with the endoxylanase mutant to produce the enzyme composition, or a product obtained by purifying and formulating the culture solution may be used in combination with the endoxylanase mutant to produce the enzyme composition.

The filamentous fungus to produce the additional enzyme is preferably a filamentous fungus belonging to *Trichoderma*. More preferably, a cellulase mixture derived from *Trichoderma reesei*, among *Trichoderma*, can be used. Examples of cellulase mixtures derived from *Trichoderma reesei* include cellulase mixtures derived from *Trichoderma reesei* QM9414, *Trichoderma reesei* QM9123, *Trichoderma reesei* RutC-30, *Trichoderma reesei* PC3-7, *Trichoderma reesei* CL-847, *Trichoderma reesei* MCG77, *Trichoderma reesei* MCG80, and *Trichoderma viride* QM9123. Alternatively, a mutant strain may be used which belongs to *Trichoderma* and has improved cellulase productivity through mutagenesis treatment with a mutagen, UV irradiation or the like.

Moreover, a material other than enzymes such as a protease inhibitor, a dispersant, a solubility enhancer, a stabilizer, a buffer, and a preservative may be added to the enzyme composition for biomass decomposition.

The enzyme composition for biomass decomposition can be used in a method of producing a sugar solution by adding to biomass. "Sugar solution" refers to a solution at least containing a saccharide formed through hydrolysis of a polysaccharide derived from biomass into a saccharide with a lower molecular weight. Examples of sugar components in a sugar solution include xylose, glucose, cellobiose, xylobiose, xylotriose, xylotetraose, xylopentaose, mannose, arabinose, sucrose, and fructose. Due to that the enzyme composition for biomass decomposition at least contains the endoxylanase mutant, a sugar solution obtained by using the enzyme composition contains xylose, xylobiose, xylotriose, xylotetraose, and xylopentaose in many cases. Biomass used for production of a sugar solution may be any of the above-described biomasses, and biomass pretreated for the purpose of increasing sugar yield from the biomass can be preferably used. "Pretreatment" refers to a process of partially decomposing lignin and hemicellulose in biomass by using an acid, an alkali, pressurized hot water or the like, in advance. In the method of producing a sugar solution, the enzyme composition for biomass decomposition is added to biomass, and preferably reacted under conditions of a temperature of 40° C. to 100° C., a treatment pH of 3 to 7, and a biomass concentration of 0.1 to 30% for 1 minute to 240 hours. Setting those parameters in the range can maximize the decomposition efficiency of the enzyme composition for biomass decomposition.

The enzyme composition for biomass decomposition used in the method of producing a sugar solution can be recovered and further reused. The endoxylanase mutant contained in the recovered enzyme composition for biomass decomposition can retain 50% or higher, 60% or higher, 70% or higher, or 80% or higher, preferably 90% or higher, of the activity before being used in the method of producing a sugar solution. Recovery of the enzyme composition for biomass decomposition can be performed by using the following method. The enzyme composition for biomass decomposition is added to biomass for hydrolysis reaction, and the hydrolyzate is then subjected to solid-liquid separation. The solution component obtained by the solid-liquid separation contains the enzyme composition for biomass decomposition and sugar components, and the enzyme composition for biomass decomposition and the sugar components are separated through filtration with an ultrafiltration membrane. In the separation of the enzyme composition for biomass decomposition and the sugar components with an ultrafiltration membrane, the cut-off molecular weight is not limited and may be any cut-off molecular weight such that monosaccharides and oligosaccharides (2 to 10 sugar units) are transmitted and the enzyme composition for biomass decomposition is blocked. Specifically, the cut-off molecular weight is only required to be 2,000 to 50,000, and more preferably 5,000 to 50,000, and further preferably 10,000 to 30,000 from the viewpoint of separation of contaminants having inhibiting action for enzymatic reaction from the enzyme. Examples of materials applicable to the ultrafiltration membrane include polyethersulfone (PES), polysulfone (PS), polyacrylonitrile (PAN), polyvinylidene fluoride (PVDF), regenerated cellulose, cellulose, cellulose ester, sulfonated polysulfone, sulfonated polyethersulfone, polyolefin, polyvinyl alcohol, polymethyl methacrylate, and polytetrafluoroethylene, and it is preferred to use an ultrafiltration membrane the material of which is synthesized polymer such as PES and PVDF. In recovery and/or reuse of the enzyme composition for biomass decomposition, the endoxylanase mutant contained in the enzyme composition for biomass decomposition is more preferably an endoxylanase mutant comprising the amino acid sequence of SEQ ID NO: 10, which is an amino acid sequence being the amino acid sequence of SEQ ID NO: 1 including substitution of an amino acid at nine positions of position 35, position 44, position 62, position 63, position 101, position 102, position 61, position 65, and position 66.

Since a sugar solution obtained by using the method of producing a sugar solution contains a monosaccharide component such as glucose and xylose, the sugar solution can be used for a raw material sugar of ethanol, lactic acid and the like. Since a sugar solution obtained by using the method of producing a sugar solution contains xylooligosaccharide, xylobiose, xylotriose or the like, the sugar solution can be used as an oligosaccharide for prebiotics, and can be used for health foods for humans and livestock feed.

EXAMPLES

Hereinafter, our enzymes, compositions and methods will be specifically described with reference to Examples. However, this disclosure is never limited thereto.

Reference Example 1 Measurement of Protein Concentration

The protein concentration of each of endoxylanases and endoxylanase mutants was measured by using a BCA method. 25 µL of a solution containing endoxylanase or an endoxylanase mutant was mixed with 200 µL of a BCA reagent, and reacted at 37° C. for 30 minutes to allow the mixture to develop color. The mixture was subjected to measurement of absorbance at 570 nm and colorimetry with bovine serum albumin as a reference standard to determine the protein concentration.

Reference Example 2 Preparation of Trichoderma-Derived Cellulase

Trichoderma-derived cellulase was prepared in accordance with the following method. Pre-culture The following materials were added to distilled water to reach the presented concentrations: corn steep liquor: 5% (w/vol), glucose: 2% (w/vol), ammonium tartrate: 0.37% (w/vol), ammonium sulfate: 0.14% (w/vol), potassium dihydrogen phosphate: 0.2% (w/vol), calcium chloride dihydrate: 0.03% (w/vol), magnesium sulfate heptahydrate: 0.03% (w/vol), zinc chloride: 0.02% (w/vol), iron (III) chloride hexahydrate: 0.01% (w/vol), copper (II) sulfate pentahydrate: 0.004% (w/vol), manganese chloride tetrahydrate: 0.0008% (w/vol), boric acid: 0.0006% (w/vol), and hexaammonium heptamolybdate tetrahydrate: 0.0026% (w/vol). In a 500 mL conical flask with baffles, 100 mL of the resultant was placed and subjected to autoclave sterilization at 121° C. for 15 minutes. After allowing to cool, PE-M and Tween 80 each having been separately subjected to autoclave sterilization at 121° C. for 15 minutes were added thereto each at a concentration of 0.01% (w/vol). On this medium for pre-culture, Trichoderma reesei ATCC 66589 (obtained from ATCC) was inoculated to reach $1\times10^5$ cells/mL, and subjected to shaking culture at 180 rpm at 28° C. for 72 hours as pre-culture (shaker: BIO-SHAKER BR-40LF manufactured by TAITEC CORPORATION).

Main Culture

The following materials were added to distilled water to reach the presented concentrations: corn steep liquor: 5% (w/vol), glucose: 2% (w/vol), cellulose (Avicel): 10% (w/vol), ammonium tartrate: 0.37% (w/vol), ammonium sulfate 0.14% (w/vol), potassium dihydrogen phosphate: 0.2% (w/vol), calcium chloride dihydrate: 0.03% (w/vol), magnesium sulfate heptahydrate: 0.03% (w/vol), zinc chloride: 0.02% (w/vol), iron (III) chloride hexahydrate: 0.01% (w/vol), copper (II) sulfate pentahydrate: 0.004% (w/vol), manganese chloride tetrahydrate: 0.0008% (w/vol), boric acid: 0.0006% (w/vol), and hexaammonium heptamolybdate tetrahydrate: 0.0026% (w/vol). In a 5 L stirring jar (DPC-2A manufactured by ABLE Corporation), 2.5 L of the resultant was placed and subjected to autoclave sterilization at 121° C. for 15 minutes. After allowing to cool, PE-M and Tween 80 each having been separately subjected to autoclave sterilization at 121° C. for 15 minutes were added thereto each at a concentration of 0.1%, and thereon 250 mL of Trichoderma reesei PC3-7 pre-cultured in advance in a liquid medium in accordance with the above method was inoculated. Thereafter, culturing was performed at 300 rpm at 28° C. for 87 hours by using an aeration rate of 1 vvm, and the culture was centrifuged and the supernatant was then subjected to membrane filtration (Stericup-GV manufactured by Millipore Corporation, material: PVDF). To the culture solution prepared under the conditions, β-glucosidase (Novozyme 188) was added at a protein weight ratio of 1/100, and the resultant was used as *Trichoderma*-derived cellulase in the following Examples. Comparative Example 1 Cloning of Wild-type endoxylanase (having amino acid sequence of SEQ ID NO: 1) isolated from *Acremonium cellulolyticus*

A DNA encoding wild-type endoxylanase having the amino acid sequence of SEQ ID NO: 1 was isolated from an *Acremonium cellulolyticus* CF strain by using RT-PCR, and a DNA including the nucleotide sequence of SEQ ID NO: 33 encoding a protein obtained by removing the signal peptide region from the wild-type endoxylanase was cloned into the NdeI site and BamHI site of a pET11a (Novagen). "ATG" in the nucleotide sequence CATATG at the NdeI site of the pET11a was used for a translation start site as a methionine codon, and the stop codon "TAG" was included at the 3'-terminal.

The pET11a including the nucleotide sequence of SEQ ID NO: 33 was cloned into a BL21 (DE3) strain (Novagen). The recombinant BL21 (DE3) strain obtained was cultured in an LB medium containing 100 mg/L of ampicillin sodium at 37° C. until the OD600 reached 0.6, and 200 μM of isopropyl-β-D-1-thiogalactopyranoside (IPTG) was then added thereto to perform expression induction for wild-type endoxylanase having the amino acid sequence of SEQ ID NO: 2. In the expression induction, the temperature of the medium was kept at 16° C. for 20 hours. Thereafter, the bacterial cells of the recombinant BL21 (DE3) strain were collected through centrifugation at 5,000×g at 4° C. for 15 minutes. The bacterial cells collected were resuspended in a Tris buffer solution at pH 8 (20 mM Tris HCl, 50 mM NaCl). The buffer solution containing the bacterial cells was subjected to three cycles in total in each of which the buffer solution was completely frozen at −80° C. for 1 hour and then thawed at room temperature, and thus soluble proteins in the bacterial cells were extracted into the buffer solution. Thereafter, the buffer solution was centrifuged at 18,000 rpm at 4° C. for 20 minutes to separate into the supernatant and bacterial cell residue. The supernatant was allowed to pass through a Q-HP column (GE Healthcare Life Sciences) equilibrated with a Tris buffer solution (20 mM, pH 8) in advance to allow endoxylanase of interest to be adsorbed on the column, and then eluted by using the concentration gradient of NaCl. When the concentration of NaCl was 200 to 400 mM, the solution was collected as an endoxylanase fraction. Thereafter, the endoxylanase fraction was further dialyzed with a Tris buffer solution (20 mM, pH 8, 2 M NaCl), and then allowed to pass through a Butyl HP column (GE Healthcare Life Sciences) for adsorption of endoxylanase. The endoxylanase was eluted by using the concentration gradient of NaCl, and a fraction eluted at 1 M NaCl was collected. The fraction was further allowed to pass through a Superdex200 16/60 gel filtration column (GE Healthcare Life Sciences) for purification. The resulting purified endoxylanase was screened for impurities by using SDS-PAGE.

Example 1 Preparation of DNA Encoding Endoxylanase Mutant Including Substitution at any One Position of Position 35, Position 44, Position 62, Position 63, Position 101, and Position 102, and Recombinant Expression Thereof with *Escherichia coli*

As Example, each DNA encoding an endoxylanase mutant including substitution at any one position of position 35, position 44, position 62, position 63, position 101, and position 102 was prepared in accordance with the following procedure.

A pET11a (Comparative Example 1) comprising a nucleotide sequence (SEQ ID NO: 33) encoding an amino acid sequence (SEQ ID NO: 2), which is obtained by removing a signal peptide consisting of 34 amino acid residues from the N-terminal of wild-type endoxylanase, as a template, was subjected to PCR by using a primer pair listed in Table 1 (Fw: forward primer, Rv: reverse primer) to prepare a DNA encoding an endoxylanase mutant including substitution of an amino acid at a specified position. In the PCR, a PrimeSTAR MaxDNA Polymerase kit (Takara Bio Inc.) was used. The primer pairs (SEQ ID NO: 14 to SEQ ID NO: 25) used are listed in Table 1. The nucleotide sequences of the resulting DNAs each encoding an endoxylanase mutant (starting point: amino acid at position 35) are set forth in SEQ ID NO: 34, SEQ ID NO: 35, SEQ ID NO: 36, SEQ ID NO: 37, SEQ ID NO: 38, and SEQ ID NO: 39 (Table 1). The amino acid sequences of the endoxylanase mutants are set forth in SEQ ID NO: 3, SEQ ID NO: 4, SEQ ID NO: 5, SEQ ID NO: 6, SEQ ID NO: 7, and SEQ ID NO: 8. Each of the thus-obtained DNAs encoding an endoxylanase mutant was cloned into a pET11a in accordance with the procedure in Comparative Example 1. Subsequently, expression and purification of a protein was performed for each pET11a comprising the DNA encoding an endoxylanase mutant in accordance with the procedure in Comparative Example 1, and thus each endoxylanase mutant was obtained.

TABLE 1

Primer pairs for mutagenesis used in Example 1 and corresponding endoxylanase mutants (amino acid sequence and nucleotide sequence) Each underline indicates a mutated portion.

| Position | Amino acid before substitution | Amino acid after substitution | Fw/Rv | Primer nucleotide sequence (5'→3') | | Endoxylanase mutant Amino acid sequence | Nucleotide sequence |
|---|---|---|---|---|---|---|---|
| Position 35 | serine | cysteine | Fw | GATATACACATATGTGTATCACGACGAGC | SEQ ID NO: 14 | SEQ ID NO: 3 | SEQ ID NO: 34 |
| | | | Rv | GCTCGTCGTGATACACATATGTGTATATC | SEQ ID NO: 15 | | |
| Position 44 | asparagine | histidine | Fw | ACTGGGACGCCACAACGGCTACTACTACTCG | SEQ ID NO: 16 | SEQ ID NO: 4 | SEQ ID NO: 35 |
| | | | Rv | CGAGTAGTAGTAGCCGTTGTGCGTCCCAG | SEQ ID NO: 17 | | |
| Position 62 | threonine | cysteine | Fw | GTCACCTACTGTAATGGTGACAATGGCG | SEQ ID NO: 18 | SEQ ID NO: 5 | SEQ ID NO: 36 |
| | | | Rv | TTCGCCATTGTCACCATTACAGTAGGTGAC | SEQ ID NO: 19 | | |
| Position 63 | asparagine | leucine | Fw | ACCTACACATTAGGTGACAATGGCGAATAC | SEQ ID NO: 20 | SEQ ID NO: 6 | SEQ ID NO: 37 |
| | | | Rv | GTATTCGCCATTGTCACCTAATGTGTAGG | SEQ ID NO: 21 | | |
| Position 101 | threonine | proline | Fw | GGAGAATTTAATCCCAGCCGGAAACGCT | SEQ ID NO: 22 | SEQ ID NO: 7 | SEQ ID NO: 38 |
| | | | Rv | AGCGTTTCCGCTGGGATTAAATTCTCC | SEQ ID NO: 23 | | |
| Position 102 | serine | asparagine | Fw | GAATTTAATACAAACGGAAACGCTTAT | SEQ ID NO: 24 | SEQ ID NO: 8 | SEQ ID NO: 39 |
| | | | Rv | ATAAGCGTTTCCGTTTGTATTAAATTC | SEQ ID NO: 25 | | |

Example 2 Preparation of DNA Encoding Endoxylanase Mutant Including Substitution at Two Positions of Position 35 and Position 62, and Recombinant Expression Thereof with *Escherichia coli*

A DNA (SEQ ID NO: 40) encoding an endoxylanase mutant including substitution with cysteine at two positions of position 35 and position 62 was prepared by using a primer pair (SEQ ID NO: 18 and SEQ ID NO: 19) to introduce additional mutation at position 62 for the pET11 comprising a DNA encoding an endoxylanase mutant (SEQ ID NO: 3) including mutation introduced at position 35, which had been prepared in Example 1. Two primer pairs listed in Table 2 were used for the mutagenesis. The nucleotide sequence of the thus-prepared DNA encoding an endoxylanase mutant is set forth in SEQ ID NO: 9. The resulting DNA encoding an endoxylanase mutant was cloned into a pET11a in accordance with the procedure in Comparative Example 1. Subsequently, expression and purification of a protein was performed for the pET11a comprising the DNA encoding an endoxylanase mutant in accordance with the procedure in Comparative Example 1, and thus the endoxylanase mutant of Example 2 (SEQ ID NO: 9) was obtained.

TABLE 2

Primer pairs for mutagenesis used in Example 2 and corresponding endoxylanase mutant (amino acid sequence and nucleotide sequence) Each underline indicates a mutated portion.

| Position | Amino acid before substitution | Amino acid after substitution | Fw/Rv | Primer nucleotide sequence (5'→3') | | Endoxylanase mutant Amino acid sequence | Endoxylanase mutant Nucleotide sequence |
|---|---|---|---|---|---|---|---|
| Position 35 | serine | cysteine | Fw | GATATACATATGTGTATCACGACGAGC | SEQ ID NO: 14 | SEQ ID NO: 9 | SEQ ID NO: 40 |
|  |  |  | Rv | GCTCGTCGTGATACACATATGTATATC | SEQ ID NO: 15 |  |  |
| Position 62 | threonine | cysteine | Fw | GTCACCTACTGTAATGGTGACAATGGCG | SEQ ID NO: 18 |  |  |
|  |  |  | Rv | TTCGCCATTGTCACCATTACAGTAGGTGAC | SEQ ID NO: 19 |  |  |

Comparative Example 2 Preparation of DNA Encoding Endoxylanase Mutant Including Substitution at any One Position of Position 61, Position 65, and Position 66, and Recombinant Expression Thereof with *Escherichia coli*

As Comparative Example, each endoxylanase mutant including substitution at any one position of position 61, position 65, and position 66 was prepared. A pET11a comprising the nucleotide sequence (SEQ ID NO: 2) of wild-type endoxylanase as a template was subjected to PCR by using a primer pair listed in Table 3 (Fw: forward primer, Rv: reverse primer) to prepare each DNA encoding an endoxylanase mutant. In the PCR, a PrimeSTAR MaxDNA Polymerase kit (Takara Bio Inc.) was used. The nucleotide sequences of the primer pairs used are shown and the resulting DNAs encoding an endoxylanase mutant are set forth in SEQ ID NO: 42, SEQ ID NO: 43, and SEQ ID NO: 44 (Table 3). The amino acid sequences of the endoxylanase mutants are set forth in SEQ ID NO: 11, SEQ ID NO: 12, and SEQ ID NO: 13 (excluding the initial methionine). Each of the thus-obtained DNAs encoding an endoxylanase mutant was cloned into a pET11a in accordance with the procedure in Comparative Example 1. Subsequently, expression and purification of a protein was performed for each pET11a comprising the DNA encoding an endoxylanase mutant in accordance with the procedure in Comparative Example 1, and thus each of the endoxylanase mutants of Comparative Example 2 was obtained.

TABLE 3

Primer pairs for mutagenesis used in Comparative Example 2 and corresponding mutants (amino acid sequence and nucleotide sequence) Each underline indicates a mutated portion.

| Position | Amino acid before substitution | Amino acid after substitution | Fw/Rv | Primer nucleotide sequence (5'→3') | | Endoxylanase mutant | |
|---|---|---|---|---|---|---|---|
| | | | | | | Amino acid sequence | Nucleotide sequence |
| Position 61 | tyrosine | methionine | Fw | GAAGTCACCATGACAAATGGTGACAATGGC | SEQ ID NO: 26 | SEQ ID NO: 11 | SEQ ID NO: 42 |
| | | | Rv | GCCATTGTCACCATTTGTCATGGTGACTTC | SEQ ID NO: 27 | | |
| Position 65 | asparagine acid | proline | Fw | CCTACACAAATGGTCCTAACGGCGAATAC | SEQ ID NO: 28 | SEQ ID NO: 12 | SEQ ID NO: 43 |
| | | | Rv | GTATTCGCCGTTAGGACCATTTCTGTAGG | SEQ ID NO: 29 | | |
| Position 66 | asparagine | glycine | Fw | ACAAATGGTGATGGAGGCGAATACAGC | SEQ ID NO: 30 | SEQ ID NO: 13 | SEQ ID NO: 44 |
| | | | Rv | GCTGTATTCGCCTCCATCACCATTTGT | SEQ ID NO: 31 | | |

Example 3 Preparation of DNA Encoding Endoxylanase Mutant Including Substitution at Nine Positions of Position 35, Position 44, Position 62, Position 63, Position 101, Position 102, Position 61, Position 65, and Position 66, and Recombinant Expression Thereof with *Escherichia coli*

A DNA encoding an endoxylanase mutant including substitution at the specified positions was prepared by using a primer pair to introduce additional mutation at position 44, position 63, position 101, position 102, position 61, position 65, and position 66 for the pET11 comprising a DNA (SEQ ID NO: 40) encoding an endoxylanase mutant including substitution with cysteine at two positions of position 35 and position 62, which had been prepared in Example 2. Nine primer pairs listed in Table 4 were used for the mutagenesis. The nucleotide sequence of the thus-prepared DNA encoding an endoxylanase mutant is set forth in SEQ ID NO: 41. The amino acid sequence of the corresponding endoxylanase mutant is set forth in SEQ ID NO: 10. The resulting DNA encoding an endoxylanase mutant was cloned into a pET11a in accordance with the procedure in Comparative Example 1. Subsequently, expression and purification of a protein was performed for the pET11a comprising the DNA encoding an endoxylanase mutant in accordance with the procedure in Comparative Example 1, and thus the endoxylanase mutant of Example 3 (SEQ ID NO: 10) was obtained.

TABLE 4

Primer pairs for mutagenesis used in Example 3 and corresponding endoxylanase mutant (amino acid sequence and nucleotide sequence) Each underline indicates a mutated portion.

| Position | Amino acid before substitution | Amino acid after substitution | Fw/Rv | Primer nucleotide sequence (5'→3') | | Endoxylanase mutant Amino acid sequence | Nucleotide sequence |
|---|---|---|---|---|---|---|---|
| Position 35 | serine | cysteine | Fw | GATATACATATGTGTATCACGACGAGC | SEQ ID NO: 14 | SEQ ID NO: 10 | SEQ ID NO: 41 |
|  |  |  | Rv | GCTCGTCGTGATACACATATGTATATC | SEQ ID NO: 15 |  |  |
| Position 44 | asparagine | histidine | Fw | ACTGGGACGCACAACGGCTACTACTCG | SEQ ID NO: 16 |  |  |
|  |  |  | Rv | CGAGTAGTAGCCGTTGTGCGTCCCAG | SEQ ID NO: 17 |  |  |
| Position 62 | threonine | cysteine | Fw | GTCACCTACTGTAATGGTGACAATGGCG | SEQ ID NO: 18 |  |  |
|  |  |  | Rv | TTCGCCATTGTCACCATTACAGTAGGTGAC | SEQ ID NO: 19 |  |  |
| Position 63 | asparagine | leucine | Fw | ACCTACACATTAGGTGACAATGGCGAATAC | SEQ ID NO: 20 |  |  |
|  |  |  | Rv | GTATTCGCCATTGTCACCTAATGTGTAGG | SEQ ID NO: 21 |  |  |
| Position 101 | threonine | proline | Fw | GGAGAATTTAATCCCAGCGGAAACGCT | SEQ ID NO: 22 |  |  |
|  |  |  | Rv | AGCGTTTCCGCTGGGATTAAATTCTCC | SEQ ID NO: 23 |  |  |
| Position 102 | serine | asparagine | Fw | GAATTTAATACAAACGGAAACGCTTAT | SEQ ID NO: 24 |  |  |
|  |  |  | Rv | ATAAGCGTTTCCGTTTGTATTAAATTC | SEQ ID NO: 25 |  |  |
| Position 61 | tyrosine | methionine | Fw | GAAGTCACCATGACAAATGGTGACAATGGC | SEQ ID NO: 26 |  |  |
|  |  |  | Rv | GCCATTGTCACCATTTGTCATGGTGACTTC | SEQ ID NO: 27 |  |  |
| Position 65 | asparagine acid | proline | Fw | CCTACACAAATGGTCCTAACGGCGAATAC | SEQ ID NO: 28 |  |  |
|  |  |  | Rv | GTATTCGCCGTTAGGACCATTTGTGTAGG | SEQ ID NO: 29 |  |  |
| Position 66 | asparagine | glycine | Fw | ACAAATGGTGATGGAGGCGAATACAGC | SEQ ID NO: 30 |  |  |
|  |  |  | Rv | GCTGTATTCGCCTCCATCACCATTTGT | SEQ ID NO: 31 |  |  |

Example 4 Measurement of Endoxylanase Activity for Endoxylanase Mutants of Examples 1 to 3, Wild-Type Endoxylanase of Comparative Example 1, and Endoxylanase Mutants of Comparative Example 2 at Different Temperatures Endoxylanase activity was measured by using 1% Birchwood xylan (Sigma Aldrich Co. LLC.) as a substrate. The quantity of a reducing sugar generated through hydrolysis of Birchwood xylan by endoxylanase was measured by using a dinitrosalicylic acid method (DNS method) with xylose as a reference standard. For the reaction, each of the endoxylanase mutants (Example 1, Example 2, and Example 3), wild-type endoxylanase (Comparative Example 1), and endoxylanase mutants (Comparative Example 2) was added to reach 1 mg/mL, and the temperature was kept at a temperature of 50° C., 55° C., 60° C., 65° C., or 70° C. for 10 minutes to decompose the Birchwood xylan. The protein concentration was adjusted through concentration measurement in accordance with Reference Example 1. After the reaction, 0.75 mL of a DNS solution was added to initiate reaction for measurement of the quantity of a reducing sugar, and the resultant was boiled for 5 minutes to terminate the reaction. The absorbance of the reaction solution after the termination of the reaction at 540 nm was measured to determine the quantity of a reducing sugar. Under the definition that 1 unit of endoxylanase activity corresponds to the quantity of an enzyme required to generate 1 μmol of xylose from Birchwood xylan at 50° C. in 1 minute, the value in units was calculated. Activity values relative to the activity value of the wild-type (Comparative Example 1) at 55° C. as a reference (100%) were obtained on the basis of the values in units calculated. The relative activity values are summarized in Table 5.

The results revealed that the endoxylanase mutants each including substitution at a position or positions selected from position 35, position 44, position 62, position 63, position 101, and position 102 retained high activity in contrast to the wild-type endoxylanase even under high temperature conditions, and thus the mutation enhanced the thermal resistance. The endoxylanase mutant including substitution at position 35, position 44, position 62, position 63, position 101, and position 102, and further at position 61, position 65, and position 66 was found to have particularly high thermal resistance.

TABLE 5

Relative activity values for decomposition of Birchwood xylan at different temperatures
A Bold italic number corresponds to high thermal resistance.

|  | 50° C. | 55° C. | 60° C. | 65° C. | 70° C. |
|---|---|---|---|---|---|
| Wild-type (Comparative Example 1) | 97 | 100 | 99 | 16 | 11 |
| T101P (Example 1) | 94 | 97 | 108 | *41* | *41* |
| S102N (Example 1) | 97 | 99 | 115 | *52* | *32* |
| N44H (Example 1) | 103 | 101 | 107 | *67* | *25* |
| S35C (Example 1) | 87 | 80 | 79 | *80* | *36* |
| T62C (Example 1) | 90 | 98 | 103 | *104* | *88* |
| S35C (Example 1) | 87 | 80 | 79 | *80* | *36* |
| S35C/T62C (Example 2) | 105 | 122 | 147 | *154* | *150* |
| S35C/N44H/Y61M/T62C/N63L/T101P/S102N/D65P/N66G (Example 3) | 114 | 133 | 169 | *177* | *189* |
| Y61M (Comparative Example 2) | 88 | 73 | 22 | 11 | 17 |

TABLE 5-continued

Relative activity values for decomposition of Birchwood xylan at different temperatures
A Bold italic number corresponds to high thermal resistance.

|  | 50° C. | 55° C. | 60° C. | 65° C. | 70° C. |
|---|---|---|---|---|---|
| D65P (Comparative Example 2) | 88 | 67 | 31 | 16 | 14 |
| N63L (Comparative Example 2) | 81 | 71 | 32 | 16 | 14 |
| N66G (Comparative Example 2) | 84 | 67 | 35 | 15 | 11 |

Example 5 Method 1 of Producing Sugar Solution by Using Endoxylanase Mutant

Production of an oligosaccharide solution was attempted by using bagasse, which is a residue after extraction of sugarcane juice, as a raw material. For endoxylanase, the wild-type endoxylanase of Comparative Example 1 or the endoxylanase mutant of Example 3 was used. For pretreatment, the biomass was immersed in a 1 N aqueous solution of caustic soda for 6 days so that the weight of the biomass reached 30% (w/w). The pretreated product was weighed in portions of 0.5 g into a 2 mL tube, and water was added thereto so that the final concentration of the biomass was 10% (w/w), and the pH was then adjusted to pH 5 with dilute sulfuric acid. To the composition after pH adjustment, 0.05 mg/g-BM of the wild-type endoxylanase or endoxylanase mutant was added, and the resultant was reacted by using a thermoblock rotator (SN-48BN manufactured by Nissin Rika) at 50° C. for 24 hours. The sugar composition of the supernatant after the reaction is shown in Table 6. In the endoxylanase mutant, xylobiose, which is a xylooligosaccharide, was obtained in a larger quantity than in the wild-type endoxylanase.

TABLE 6

Production 1 of sugar solution by using endoxylanase mutant

|  | Xylobiose |
|---|---|
| Wild-type (Comparative Example 1) | 3.5 g/L |
| Mutant (Example 3) | 6.9 g/L |

Example 6 Method 2 of Producing Sugar Solution by Using Endoxylanase Mutant

Production of a sugar solution was attempted as in Example 5 by using the *Trichoderma*-derived cellulase (Reference Example 2) as an enzyme in addition to the endoxylanase mutant. In the same manner as in Example 5, a composition after pH adjustment was obtained, and the *Trichoderma*-derived cellulase and the endoxylanase mutant (Example 3) were added to the composition at 10 mg/g-BM, in terms of the amount of a protein, and 0.05 mg/g-BM, respectively, and the resultant was reacted by using a thermoblock rotator (SN-48BN manufactured by Nissin Rika) at 50° C. for 48 hours. For comparison, reaction was performed with addition of only the *Trichoderma*-derived cellulase. The sugar composition of the supernatant after the reaction is shown in Table 7. Addition of the endoxylanase mutant in addition to the *Trichoderma*-derived cellulase provided more enhanced sugar yield than addition of only the *Trichoderma*-derived cellulase.

TABLE 7

Production 2 of sugar solution by using endoxylanase mutant

|  | Glucose | Xylose |
|---|---|---|
| Cellulase (Reference Example 2) | 32.9 g/L | 21.0 g/L |
| Cellulase (Reference Example 2) + Mutant (Example 3) | 35.0 g/L | 22.3 g/L |

Example 7 Residual Endoxylanase Activity after Reaction in Example 5

By using a VIVASPIN500 (PES, cut-off molecular weight: 10,000) (Sartorius), 500 µL of the supernatant after the reaction obtained in Example 5 was subjected to ultrafiltration to collect the wild-type endoxylanase of Comparative Example 1 or the endoxylanase mutant of Example 3. Endoxylanase activity was measured for the wild-type endoxylanase of Comparative Example 1 or the endoxylanase mutant of Example 3 collected, and the wild-type endoxylanase of Comparative Example 1 or the endoxylanase mutant of Example 3 diluted to the concentration at xylanolysis (2.5 mg/L). Measurement of endoxylanase activity was performed in the same manner as in Example 4 except that the collected endoxylanase or diluted endoxylanase in 1/10 of the quantity of the reaction solution was added and the reaction temperature was 50° C. By using the activity values for the wild-type endoxylanase of Comparative Example 1 and endoxylanase mutant of Example 3 diluted as a reference (100%), the relative activity values for the wild-type endoxylanase of Comparative Example 1 and endoxylanase mutant of Example 3 collected were determined, respectively, which were used as the residual activity. Table 8 shows the residual activity after collection. In the case of the endoxylanase mutant, high activity remained even after xylanolysis, and it was demonstrated that the endoxylanase mutant can be significantly reused for xylanolysis.

TABLE 8

Residual activity after xylanolysis by using endoxylanase mutant

|  | Residual activity |
|---|---|
| Wild-type (Comparative Example 1) | 7% |
| Mutant (Example 3) | 94% |

Example 8 Expression of Wild-Type Endoxylanase and Endoxylanase Mutant by Using Yeast *Pichia pastoris*

The pET11a (Comparative Example 1) comprising a nucleotide sequence (SEQ ID NO: 33) encoding an amino acid sequence (SEQ ID NO: 2), which is obtained by removing a signal peptide consisting of 34 amino acid residues from the N-terminal of wild-type endoxylanase, as a template, was subjected to PCR by using a primer pair of SEQ ID NO: 51 and SEQ ID NO: 53 to prepare a DNA encoding SEQ ID NO: 54, SEQ ID NO: 47, and SEQ ID NO: 55 in the order presented.

The pET11a (Example 3) comprising a DNA (SEQ ID NO: 41) encoding an endoxylanase mutant (SEQ ID NO: 10) including substitution at nine positions of position 35, position 44, position 62, position 63, position 101, position 102, position 61, position 65, and position 66, as a template, was subjected to PCR by using a primer pair of SEQ ID NO: 52 and SEQ ID NO: 53 to prepare a DNA encoding SEQ ID NO: 54, SEQ ID NO: 50, and SEQ ID NO: 55 in the order presented. In the PCR, a PrimeSTAR MaxDNA Polymerase kit (Takara Bio Inc.) was used.

Further, artificial gene synthesis was performed to synthesize a DNA including addition of the nucleotide sequence of SEQ ID NO: 54 and the nucleotide sequence of SEQ ID NO: 55 to the upstream and downstream, respectively, of a nucleotide sequence (SEQ ID NO: 48) encoding an endoxylanase mutant (SEQ ID NO: 9) including substitution at two positions of position 35 and position 62, and a DNA including addition of the nucleotide sequence of SEQ ID NO: 54 and the nucleotide sequence of SEQ ID NO: 55 to the upstream and downstream, respectively, of a nucleotide sequence (SEQ ID NO: 49) encoding an endoxylanase mutant (SEQ ID NO: 45) including substitution at seven positions of position 35, position 44, position 62, position 63, position 61, position 65, and position 66. The two DNAs obtained through the PCR and the two DNAs obtained through the artificial gene synthesis, i.e., four DNAs in total, were cleaved at the SapI site with an Electra Vector System from DNA2.0 to clone into a pD915. Each of the four DNAs was cloned into the downstream of the nucleotide sequence of SEQ ID NO: 56, and thus obtained were plasmids each comprising a DNA encoding a protein including addition of a secretion signal peptide region (SEQ ID NO: 46) at the N-terminal of SEQ ID NO: 2, 10, 9, or 45.

Competent cells of a *Pichia pastoris* PPS-9010 strain (DNA2.0) were prepared. A single colony of a *Pichia pastoris* PPS-9010 strain was inoculated in a 100 mL flask containing 20 mL of a YPD liquid medium (yeast extract: 1% (w/vol), peptone: 2% (w/vol), glucose: 2% (w/vol)), and subjected to shaking culture at 120 rpm at 30° C. for 16 hours (pre-culture). The pre-culture solution was inoculated in a 200 mL flask with baffles containing 50 mL of a YPD liquid medium to achieve D600=0.15 to 0.2, and subjected to shaking culture at 120 rpm at 30° C. to proliferate until OD600=0.8 to 1.0 was achieved. The culture solution was transferred in a 50 mL Falcon tube, and the bacterial cells were collected through centrifugation at 500×g for 15 minutes. To the bacterial cells collected, 9 mL of an ice-cooled BEDS solution (10 mM Bicine-sodium hydroxide buffer solution (pH 8.3), ethylene glycol: 3% (vol/vol), dimethylsulfoxide (DMSO): 5% (vol/vol), 1 M sorbitol) was added, and the bacterial cells were gently suspended. Further, 1 mL of 1 M dithiothreitol (DTT) was added thereto, and the bacterial cells were gently suspended, and shaken at 100 rpm at 30° C. for 5 minutes. Centrifugation was performed at 500×g for 15 minutes, and 1 mL of an ice-cooled BEDS solution was added to the resulting precipitate, and the precipitate was gently suspended, which was used as competent cells. The competent cells were directly used for transformation, or dispensed into 200 µL aliquots and the aliquots were stored at −80° C.

Each of the plasmids in an amount of 20 µg was cleaved at the AvrII site to convert into linear fragments. The linear fragments were purified by using ethanol precipitation, and mixed with 50 µL of the competent cells of *Pichia pastoris*, and the resultant was then transferred in an ice-cooled electroporation cuvette (0.2 cm) (Bio-Rad Laboratories, Inc.), and the electroporation cuvette was placed on ice for 2 minutes. Electroporation was performed by using a Gene Pulser Xcell (Bio-Rad Laboratories, Inc.) at a voltage of 1.5 kV, a resistance of 200Ω, and a capacitance of 25 and immediately thereafter 0.5 mL of ice-cooled 1 M sorbitol was added thereto, and the resultant was transferred in 14 mL Falcon tubes each containing 0.5 mL of a YPD liquid medium. The Falcon tubes were subjected to shaking culture at 120 rpm at 30° C. for 1.5 hours, and 100 μL of the culture solution was applied on a Zeocin-containing YPDS plate medium (Zeocin: 1 mg/mL, yeast extract: 1% (w/vol), peptone: 2% (w/vol), glucose: 2% (w/vol), 1 M sorbitol, agar: 2% (w/vol)) with a bacteria spreader, and cultured at 30° C. for 2 to 3 days. From colonies generated on the plate, colonies having a large diameter were chosen, and the colonies were picked with a sterilized toothpick to inoculate in a 96-well plate with a capacity of 2 mL each well of which contained 0.5 mL of a YPD liquid medium, and cultured at 1000 rpm at 28° C. for 4 days. FIG. 1 shows the result of SDS-PAGE for the supernatant of the culture solution. The result confirmed that all of the proteins were secretory expressed. For each of the proteins comprising SEQ ID NOs: 2, 9, and 45, respectively, a band was detected at a position corresponding to a molecular weight higher than the molecular weight estimated from the primary structure, which confirmed that glycosylation occurred on expression in Pichia.

TABLE 9

Wild-type endoxylanase and xylanase mutant prepared in Example 8

| | | Amino acid sequence | Nucleotide sequence |
|---|---|---|---|
| 1 | Wild-type | SEQ ID NO: 2 | SEQ ID NO: 47 |
| 2 | S35C/T62C | SEQ ID NO: 9 | SEQ ID NO: 48 |
| 3 | S35C/N44H/T62C/Y61M/D65P/N83L/N66G | SEQ ID NO: 45 | SEQ ID NO: 49 |
| 4 | S35C/N44H/T62C/T101P/S102N/Y61M/D65P/N63L/N66G | SEQ ID NO: 10 | SEQ ID NO: 50 |

Example 9 Comparison of Activity Among Endoxylanase Mutants

Activity measurement of endoxylanase was performed for the supernatant of each culture solution obtained in Example 8. Activity measurement was performed in the same manner as in Example 4 except that the supernatant of each culture solution was added to reach 0.25 mg/mL and reaction was performed at temperatures of 50° C., 60° C., and 70° C. Activity values relative to the activity value of the wild-type at 50° C. as a reference (100%) were obtained on the basis of the values in units calculated. The relative activity values are summarized in Table 11. The supernatant containing a xylanase mutant retained high activity even under a high temperature condition. In addition, the enzyme expressed in the yeast was found to have higher thermal resistance than the enzyme expressed in *Escherichia coli* in Example 4.

TABLE 10

Relative activity values for decomposition of Birchwood xylan at different temperatures

| | | 50° C. | 60° C. | 70° C. |
|---|---|---|---|---|
| 1 | Wild-type | 100 | 114 | 25 |
| 2 | S35C/T62C | 101 | 155 | 183 |
| 3 | S35C/N44H/T62C/Y61M/D65P/N63L/N66G | 114 | 181 | 204 |
| 4 | S35C/N44H/T62C/T101P/S102N/Y61M/D65P/N63L/N66G | 115 | 171 | 240 |

INDUSTRIAL APPLICABILITY

The endoxylanase mutant exhibits high xylanolytic activity under high temperature conditions, and thus can be used for hydrolysis of biomass, production of a sugar solution, and production of an oligosaccharide.

All of the publications, patents, and patent applications cited herein are directly incorporated herein by citation.

The invention claimed is:

1. An endoxylanase mutant having endoxylanase activity and comprising substitutions of amino acid residues corresponding to position 35, position 44, position 62, position 63, position 61, position 65, and position 66 of SEQ ID NO: 1, wherein the amino acid sequence is obtained from a filamentous fungus.

2. The endoxylanase mutant of claim 1, wherein amino acid residues at all of positions corresponding to position 35, position 44, position 61, position 62, position 63, position 65, position 66, position 101, and position 102 of SEQ ID NO: 1 are substituted.

3. The endoxylanase mutant of claim 1, wherein an amino acid residue corresponding to position 35 and/or position 62 of SEQ ID NO: 1 is substituted with cysteine.

4. The endoxylanase mutant of claim 1, wherein an amino acid residue corresponding to position 44 and/or position 63 of SEQ ID NO: 1 is substituted with an amino acid independently, for each position, selected from histidine, glycine, tryptophan, methionine, proline, alanine, phenylalanine, valine, leucine, and isoleucine.

5. The endoxylanase mutant of claim 2, wherein an amino acid residue corresponding to position 101 and/or position 102 of SEQ ID NO: 1 is substituted with an amino acid independently, for each position, selected from proline and asparagine.

6. The endoxylanase mutant of claim 1, wherein the endoxylanase obtained from a filamentous fungus is obtained from *Acremonium cellulolyticus*.

7. The endoxylanase mutant of claim 1, having endoxylanase activity and consisting of any of:
(a) an amino acid sequence as set forth in SEQ ID NO: 10, or 45;
(b) an amino acid sequence comprising deletion, substitution, or addition of an amino acid at one to several positions without mutating a substituted amino acid or substituted amino acids at position 35, position 44, position 61, position 62, position 63, position 65, position 66, position 101, and position 102 in the amino acid sequence as set forth in SEQ ID NO: 10, or 45; and
(c) an amino acid sequence having 90% or more of sequence identity to an amino acid sequence as set forth in SEQ ID NO: 10, or 45 excluding a substituted amino acid or substituted amino acids at position 35, position 44, position 61, position 62, position 63, position 65, position 66, position 101, and position 102 without mutating the substituted amino acid or substituted amino acids.

8. An enzyme composition for biomass decomposition, the enzyme composition comprising the endoxylanase mutant of claim 1.

9. The enzyme composition of claim 8, further comprising one or more enzymes selected from the group consisting of cellobiohydrolase, endoglucanase, β-glucosidase, β-xylosidase, mannanase, mannosidase, glucoamylase, α-amylase, esterase, and lipase.

10. A method of producing a sugar solution from biomass, the method comprising adding an enzyme composition for biomass decomposition comprising the endoxylanase mutant of claim 1 to the biomass and hydrolyzing a polysaccharide derived from the biomass into a saccharide.

11. A method of producing a sugar solution from biomass, the method comprising adding an enzyme composition for biomass decomposition comprising the endoxylanase mutant of claim 1 to the biomass and hydrolyzing a polysaccharide derived from the biomass into a saccharide, wherein the enzyme composition further comprises one or more enzymes selected from the group consisting of cellobiohydrolase, endoglucanase, β-glucosidase, β-xylosidase, mannanase, mannosidase, glucoamylase, α-amylase, esterase, and lipase.

12. The endoxylanase mutant of claim 2, wherein an amino acid residue corresponding to position 35 and/or position 62 of SEQ ID NO: 1 is substituted with cysteine.

13. The endoxylanase mutant of claim 2, wherein an amino acid residue corresponding to position 44 and/or position 63 of SEQ ID NO: 1 is substituted with an amino acid independently, for each position, selected from histidine, glycine, tryptophan, methionine, proline, alanine, phenylalanine, valine, leucine, and isoleucine.

14. The endoxylanase mutant of claim 3, wherein an amino acid residue corresponding to position 44 and/or position 63 of SEQ ID NO: 1 is substituted with an amino acid independently, for each position, selected from histidine, glycine, tryptophan, methionine, proline, alanine, phenylalanine, valine, leucine, and isoleucine.

15. The endoxylanase mutant of claim 3, wherein an amino acid residue corresponding to position 101 and/or position 102 of SEQ ID NO: 1 is substituted with an amino acid independently, for each position, selected from proline and asparagine.

16. The endoxylanase mutant of claim 4, wherein an amino acid residue corresponding to position 101 and/or position 102 of SEQ ID NO: 1 is substituted with an amino acid independently, for each position, selected from proline and asparagine.

* * * * *

SEQUENCE LISTING

<160> NUMBER OF SEQ ID NOS: 56

<210> SEQ ID NO 1
<211> LENGTH: 223
<212> TYPE: PRT
<213> ORGANISM: Acremonium cellulolyticus

<400> SEQUENCE: 1

Met Lys Leu Ser Leu Ala Ala Ile Gly Ile Cys Thr Thr Ala Ala Val
1               5                   10                  15

Ala Phe Pro Ser Gly Leu Thr Gln His Ala Thr Gly Asp Leu Ser Lys
            20                  25                  30

Arg Gln Ser Ile Thr Thr Ser Gln Thr Gly Thr Asn Asn Gly Tyr Tyr
        35                  40                  45

Tyr Ser Phe Trp Thr Asn Gly Gly Gly Glu Val Thr Tyr Thr Asn Gly
    50                  55                  60

Asp Asn Gly Glu Tyr Ser Val Thr Trp Val Asn Cys Gly Asp Phe Thr
65                  70                  75                  80

Ser Gly Lys Gly Trp Asn Pro Ala Asn Ala Gln Thr Val Thr Tyr Ser
                85                  90                  95

Gly Glu Phe Asn Thr Ser Gly Asn Ala Tyr Leu Ala Val Tyr Gly Trp
            100                 105                 110

```
Thr Thr Asp Pro Leu Val Glu Tyr Ile Leu Glu Ser Tyr Gly Thr
        115                 120                 125

Tyr Asn Pro Ser Ser Gly Leu Thr Leu Leu Gly Gln Val Thr Ser Asp
    130                 135                 140

Gly Gly Thr Tyr Asp Ile Tyr Ser Thr Gln Arg Val Asp Gln Pro Ser
145                 150                 155                 160

Ile Glu Gly Thr Ser Thr Phe Asn Gln Tyr Trp Ser Val Arg Thr Glu
                165                 170                 175

Lys Arg Val Gly Gly Thr Val Thr Thr Ala Asn His Phe Ala Ala Trp
            180                 185                 190

Lys Ala Leu Gly Leu Glu Met Gly Thr Tyr Asn Tyr Met Ile Val Ser
        195                 200                 205

Thr Glu Gly Tyr Glu Ser Ser Gly Ser Ser Thr Ile Thr Val Ser
    210                 215                 220
```

<210> SEQ ID NO 2
<211> LENGTH: 189
<212> TYPE: PRT
<213> ORGANISM: Acremonium cellulolyticus

<400> SEQUENCE: 2

```
Ser Ile Thr Thr Ser Gln Thr Gly Thr Asn Asn Gly Tyr Tyr Tyr Ser
1               5                   10                  15

Phe Trp Thr Asn Gly Gly Gly Glu Val Thr Tyr Thr Asn Gly Asp Asn
                20                  25                  30

Gly Glu Tyr Ser Val Thr Trp Val Asn Cys Gly Asp Phe Thr Ser Gly
            35                  40                  45

Lys Gly Trp Asn Pro Ala Asn Ala Gln Thr Val Thr Tyr Ser Gly Glu
50                  55                  60

Phe Asn Thr Ser Gly Asn Ala Tyr Leu Ala Val Tyr Gly Trp Thr Thr
65                  70                  75                  80

Asp Pro Leu Val Glu Tyr Tyr Ile Leu Glu Ser Tyr Gly Thr Tyr Asn
                85                  90                  95

Pro Ser Ser Gly Leu Thr Leu Leu Gly Gln Val Thr Ser Asp Gly Gly
                100                 105                 110

Thr Tyr Asp Ile Tyr Ser Thr Gln Arg Val Asp Gln Pro Ser Ile Glu
            115                 120                 125

Gly Thr Ser Thr Phe Asn Gln Tyr Trp Ser Val Arg Thr Glu Lys Arg
        130                 135                 140

Val Gly Gly Thr Val Thr Thr Ala Asn His Phe Ala Ala Trp Lys Ala
145                 150                 155                 160

Leu Gly Leu Glu Met Gly Thr Tyr Asn Tyr Met Ile Val Ser Thr Glu
                165                 170                 175

Gly Tyr Glu Ser Ser Gly Ser Ser Thr Ile Thr Val Ser
            180                 185
```

<210> SEQ ID NO 3
<211> LENGTH: 189
<212> TYPE: PRT
<213> ORGANISM: Acremonium cellulolyticus

<400> SEQUENCE: 3

```
Cys Ile Thr Thr Ser Gln Thr Gly Thr Asn Asn Gly Tyr Tyr Tyr Ser
1               5                   10                  15

Phe Trp Thr Asn Gly Gly Gly Glu Val Thr Tyr Thr Asn Gly Asp Asn
                20                  25                  30
```

Gly Glu Tyr Ser Val Thr Trp Val Asn Cys Gly Asp Phe Thr Ser Gly
            35                  40                  45

Lys Gly Trp Asn Pro Ala Asn Ala Gln Thr Val Thr Tyr Ser Gly Glu
 50                  55                  60

Phe Asn Thr Ser Gly Asn Ala Tyr Leu Ala Val Tyr Gly Trp Thr Thr
 65                  70                  75                  80

Asp Pro Leu Val Glu Tyr Tyr Ile Leu Glu Ser Tyr Gly Thr Tyr Asn
                 85                  90                  95

Pro Ser Ser Gly Leu Thr Leu Leu Gly Gln Val Thr Ser Asp Gly Gly
                100                 105                 110

Thr Tyr Asp Ile Tyr Ser Thr Gln Arg Val Asp Gln Pro Ser Ile Glu
            115                 120                 125

Gly Thr Ser Thr Phe Asn Gln Tyr Trp Ser Val Arg Thr Glu Lys Arg
130                 135                 140

Val Gly Gly Thr Val Thr Thr Ala Asn His Phe Ala Ala Trp Lys Ala
145                 150                 155                 160

Leu Gly Leu Glu Met Gly Thr Tyr Asn Tyr Met Ile Val Ser Thr Glu
                165                 170                 175

Gly Tyr Glu Ser Ser Gly Ser Ser Thr Ile Thr Val Ser
                180                 185

<210> SEQ ID NO 4
<211> LENGTH: 189
<212> TYPE: PRT
<213> ORGANISM: Acremonium cellulolyticus

<400> SEQUENCE: 4

Ser Ile Thr Thr Ser Gln Thr Gly Thr His Asn Gly Tyr Tyr Tyr Ser
 1               5                  10                  15

Phe Trp Thr Asn Gly Gly Gly Glu Val Thr Tyr Thr Asn Gly Asp Asn
                 20                  25                  30

Gly Glu Tyr Ser Val Thr Trp Val Asn Cys Gly Asp Phe Thr Ser Gly
            35                  40                  45

Lys Gly Trp Asn Pro Ala Asn Ala Gln Thr Val Thr Tyr Ser Gly Glu
 50                  55                  60

Phe Asn Thr Ser Gly Asn Ala Tyr Leu Ala Val Tyr Gly Trp Thr Thr
 65                  70                  75                  80

Asp Pro Leu Val Glu Tyr Tyr Ile Leu Glu Ser Tyr Gly Thr Tyr Asn
                 85                  90                  95

Pro Ser Ser Gly Leu Thr Leu Leu Gly Gln Val Thr Ser Asp Gly Gly
                100                 105                 110

Thr Tyr Asp Ile Tyr Ser Thr Gln Arg Val Asp Gln Pro Ser Ile Glu
            115                 120                 125

Gly Thr Ser Thr Phe Asn Gln Tyr Trp Ser Val Arg Thr Glu Lys Arg
130                 135                 140

Val Gly Gly Thr Val Thr Thr Ala Asn His Phe Ala Ala Trp Lys Ala
145                 150                 155                 160

Leu Gly Leu Glu Met Gly Thr Tyr Asn Tyr Met Ile Val Ser Thr Glu
                165                 170                 175

Gly Tyr Glu Ser Ser Gly Ser Ser Thr Ile Thr Val Ser
                180                 185

<210> SEQ ID NO 5
<211> LENGTH: 189
<212> TYPE: PRT
<213> ORGANISM: Acremonium cellulolyticus

<400> SEQUENCE: 5

```
Ser Ile Thr Thr Ser Gln Thr Gly Thr Asn Asn Gly Tyr Tyr Tyr Ser
1               5                   10                  15

Phe Trp Thr Asn Gly Gly Gly Glu Val Thr Tyr Cys Asn Gly Asp Asn
            20                  25                  30

Gly Glu Tyr Ser Val Thr Trp Val Asn Cys Gly Asp Phe Thr Ser Gly
        35                  40                  45

Lys Gly Trp Asn Pro Ala Asn Ala Gln Thr Val Thr Tyr Ser Gly Glu
    50                  55                  60

Phe Asn Thr Ser Gly Asn Ala Tyr Leu Ala Val Tyr Gly Trp Thr Thr
65                  70                  75                  80

Asp Pro Leu Val Glu Tyr Tyr Ile Leu Glu Ser Tyr Gly Thr Tyr Asn
                85                  90                  95

Pro Ser Ser Gly Leu Thr Leu Leu Gly Gln Val Thr Ser Asp Gly Gly
                100                 105                 110

Thr Tyr Asp Ile Tyr Ser Thr Gln Arg Val Asp Gln Pro Ser Ile Glu
            115                 120                 125

Gly Thr Ser Thr Phe Asn Gln Tyr Trp Ser Val Arg Thr Glu Lys Arg
    130                 135                 140

Val Gly Gly Thr Val Thr Thr Ala Asn His Phe Ala Ala Trp Lys Ala
145                 150                 155                 160

Leu Gly Leu Glu Met Gly Thr Tyr Asn Tyr Met Ile Val Ser Thr Glu
                165                 170                 175

Gly Tyr Glu Ser Ser Gly Ser Ser Thr Ile Thr Val Ser
            180                 185
```

<210> SEQ ID NO 6
<211> LENGTH: 189
<212> TYPE: PRT
<213> ORGANISM: Acremonium cellulolyticus

<400> SEQUENCE: 6

```
Ser Ile Thr Thr Ser Gln Thr Gly Thr Asn Asn Gly Tyr Tyr Tyr Ser
1               5                   10                  15

Phe Trp Thr Asn Gly Gly Gly Glu Val Thr Tyr Thr Leu Gly Asp Asn
            20                  25                  30

Gly Glu Tyr Ser Val Thr Trp Val Asn Cys Gly Asp Phe Thr Ser Gly
        35                  40                  45

Lys Gly Trp Asn Pro Ala Asn Ala Gln Thr Val Thr Tyr Ser Gly Glu
    50                  55                  60

Phe Asn Thr Ser Gly Asn Ala Tyr Leu Ala Val Tyr Gly Trp Thr Thr
65                  70                  75                  80

Asp Pro Leu Val Glu Tyr Tyr Ile Leu Glu Ser Tyr Gly Thr Tyr Asn
                85                  90                  95

Pro Ser Ser Gly Leu Thr Leu Leu Gly Gln Val Thr Ser Asp Gly Gly
                100                 105                 110

Thr Tyr Asp Ile Tyr Ser Thr Gln Arg Val Asp Gln Pro Ser Ile Glu
            115                 120                 125

Gly Thr Ser Thr Phe Asn Gln Tyr Trp Ser Val Arg Thr Glu Lys Arg
    130                 135                 140

Val Gly Gly Thr Val Thr Thr Ala Asn His Phe Ala Ala Trp Lys Ala
145                 150                 155                 160

Leu Gly Leu Glu Met Gly Thr Tyr Asn Tyr Met Ile Val Ser Thr Glu
                165                 170                 175
```

Gly Tyr Glu Ser Ser Gly Ser Ser Thr Ile Thr Val Ser
            180                 185

<210> SEQ ID NO 7
<211> LENGTH: 189
<212> TYPE: PRT
<213> ORGANISM: Acremonium cellulolyticus

<400> SEQUENCE: 7

Ser Ile Thr Thr Ser Gln Thr Gly Thr Asn Asn Gly Tyr Tyr Tyr Ser
1               5                   10                  15

Phe Trp Thr Asn Gly Gly Gly Glu Val Thr Tyr Thr Asn Gly Asp Asn
                20                  25                  30

Gly Glu Tyr Ser Val Thr Trp Val Asn Cys Gly Asp Phe Thr Ser Gly
            35                  40                  45

Lys Gly Trp Asn Pro Ala Asn Ala Gln Thr Val Thr Tyr Ser Gly Glu
        50                  55                  60

Phe Asn Pro Ser Gly Asn Ala Tyr Leu Ala Val Tyr Gly Trp Thr Thr
65                  70                  75                  80

Asp Pro Leu Val Glu Tyr Tyr Ile Leu Glu Ser Tyr Gly Thr Tyr Asn
                85                  90                  95

Pro Ser Ser Gly Leu Thr Leu Leu Gly Gln Val Thr Ser Asp Gly Gly
            100                 105                 110

Thr Tyr Asp Ile Tyr Ser Thr Gln Arg Val Asp Gln Pro Ser Ile Glu
        115                 120                 125

Gly Thr Ser Thr Phe Asn Gln Tyr Trp Ser Val Arg Thr Glu Lys Arg
    130                 135                 140

Val Gly Gly Thr Val Thr Thr Ala Asn His Phe Ala Ala Trp Lys Ala
145                 150                 155                 160

Leu Gly Leu Glu Met Gly Thr Tyr Asn Tyr Met Ile Val Ser Thr Glu
                165                 170                 175

Gly Tyr Glu Ser Ser Gly Ser Ser Thr Ile Thr Val Ser
            180                 185

<210> SEQ ID NO 8
<211> LENGTH: 189
<212> TYPE: PRT
<213> ORGANISM: Acremonium cellulolyticus

<400> SEQUENCE: 8

Ser Ile Thr Thr Ser Gln Thr Gly Thr Asn Asn Gly Tyr Tyr Tyr Ser
1               5                   10                  15

Phe Trp Thr Asn Gly Gly Gly Glu Val Thr Tyr Thr Asn Gly Asp Asn
                20                  25                  30

Gly Glu Tyr Ser Val Thr Trp Val Asn Cys Gly Asp Phe Thr Ser Gly
            35                  40                  45

Lys Gly Trp Asn Pro Ala Asn Ala Gln Thr Val Thr Tyr Ser Gly Glu
        50                  55                  60

Phe Asn Thr Asn Gly Asn Ala Tyr Leu Ala Val Tyr Gly Trp Thr Thr
65                  70                  75                  80

Asp Pro Leu Val Glu Tyr Tyr Ile Leu Glu Ser Tyr Gly Thr Tyr Asn
                85                  90                  95

Pro Ser Ser Gly Leu Thr Leu Leu Gly Gln Val Thr Ser Asp Gly Gly
            100                 105                 110

Thr Tyr Asp Ile Tyr Ser Thr Gln Arg Val Asp Gln Pro Ser Ile Glu
        115                 120                 125

Gly Thr Ser Thr Phe Asn Gln Tyr Trp Ser Val Arg Thr Glu Lys Arg
            130                 135                 140

Val Gly Gly Thr Val Thr Thr Ala Asn His Phe Ala Ala Trp Lys Ala
145                 150                 155                 160

Leu Gly Leu Glu Met Gly Thr Tyr Asn Tyr Met Ile Val Ser Thr Glu
                165                 170                 175

Gly Tyr Glu Ser Ser Gly Ser Ser Thr Ile Thr Val Ser
            180                 185

<210> SEQ ID NO 9
<211> LENGTH: 189
<212> TYPE: PRT
<213> ORGANISM: Acremonium cellulolyticus

<400> SEQUENCE: 9

Cys Ile Thr Thr Ser Gln Thr Gly Thr Asn Asn Gly Tyr Tyr Tyr Ser
1               5                   10                  15

Phe Trp Thr Asn Gly Gly Gly Glu Val Thr Tyr Cys Asn Gly Asp Asn
            20                  25                  30

Gly Glu Tyr Ser Val Thr Trp Val Asn Cys Gly Asp Phe Thr Ser Gly
        35                  40                  45

Lys Gly Trp Asn Pro Ala Asn Ala Gln Thr Val Thr Tyr Ser Gly Glu
    50                  55                  60

Phe Asn Thr Ser Gly Asn Ala Tyr Leu Ala Val Tyr Gly Trp Thr Thr
65                  70                  75                  80

Asp Pro Leu Val Glu Tyr Tyr Ile Leu Glu Ser Tyr Gly Thr Tyr Asn
                85                  90                  95

Pro Ser Ser Gly Leu Thr Leu Leu Gly Gln Val Thr Ser Asp Gly Gly
            100                 105                 110

Thr Tyr Asp Ile Tyr Ser Thr Gln Arg Val Asp Gln Pro Ser Ile Glu
        115                 120                 125

Gly Thr Ser Thr Phe Asn Gln Tyr Trp Ser Val Arg Thr Glu Lys Arg
    130                 135                 140

Val Gly Gly Thr Val Thr Thr Ala Asn His Phe Ala Ala Trp Lys Ala
145                 150                 155                 160

Leu Gly Leu Glu Met Gly Thr Tyr Asn Tyr Met Ile Val Ser Thr Glu
                165                 170                 175

Gly Tyr Glu Ser Ser Gly Ser Ser Thr Ile Thr Val Ser
            180                 185

<210> SEQ ID NO 10
<211> LENGTH: 189
<212> TYPE: PRT
<213> ORGANISM: Acremonium cellulolyticus

<400> SEQUENCE: 10

Cys Ile Thr Thr Ser Gln Thr Gly Thr His Asn Gly Tyr Tyr Tyr Ser
1               5                   10                  15

Phe Trp Thr Asn Gly Gly Gly Glu Val Thr Met Cys Leu Gly Pro Gly
            20                  25                  30

Gly Glu Tyr Ser Val Thr Trp Val Asn Cys Gly Asp Phe Thr Ser Gly
        35                  40                  45

Lys Gly Trp Asn Pro Ala Asn Ala Gln Thr Val Thr Tyr Ser Gly Glu
    50                  55                  60

Phe Asn Pro Asn Gly Asn Ala Tyr Leu Ala Val Tyr Gly Trp Thr Thr
65                  70                  75                  80

```
Asp Pro Leu Val Glu Tyr Tyr Ile Leu Glu Ser Tyr Gly Thr Tyr Asn
                85                  90                  95

Pro Ser Ser Gly Leu Thr Leu Leu Gly Gln Val Thr Ser Asp Gly Gly
               100                 105                 110

Thr Tyr Asp Ile Tyr Ser Thr Gln Arg Val Asp Gln Pro Ser Ile Glu
           115                 120                 125

Gly Thr Ser Thr Phe Asn Gln Tyr Trp Ser Val Arg Thr Glu Lys Arg
       130                 135                 140

Val Gly Gly Thr Val Thr Thr Ala Asn His Phe Ala Ala Trp Lys Ala
145                 150                 155                 160

Leu Gly Leu Glu Met Gly Thr Tyr Asn Tyr Met Ile Val Ser Thr Glu
                165                 170                 175

Gly Tyr Glu Ser Ser Gly Ser Ser Thr Ile Thr Val Ser
                180                 185

<210> SEQ ID NO 11
<211> LENGTH: 189
<212> TYPE: PRT
<213> ORGANISM: Acremonium cellulolyticus

<400> SEQUENCE: 11

Ser Ile Thr Thr Ser Gln Thr Gly Thr Asn Asn Gly Tyr Tyr Tyr Ser
1               5                   10                  15

Phe Trp Thr Asn Gly Gly Gly Glu Val Thr Met Thr Asn Gly Asp Asn
                20                  25                  30

Gly Glu Tyr Ser Val Thr Trp Val Asn Cys Gly Asp Phe Thr Ser Gly
            35                  40                  45

Lys Gly Trp Asn Pro Ala Asn Ala Gln Thr Val Thr Tyr Ser Gly Glu
        50                  55                  60

Phe Asn Thr Ser Gly Asn Ala Tyr Leu Ala Val Tyr Gly Trp Thr Thr
65                  70                  75                  80

Asp Pro Leu Val Glu Tyr Tyr Ile Leu Glu Ser Tyr Gly Thr Tyr Asn
                85                  90                  95

Pro Ser Ser Gly Leu Thr Leu Leu Gly Gln Val Thr Ser Asp Gly Gly
               100                 105                 110

Thr Tyr Asp Ile Tyr Ser Thr Gln Arg Val Asp Gln Pro Ser Ile Glu
           115                 120                 125

Gly Thr Ser Thr Phe Asn Gln Tyr Trp Ser Val Arg Thr Glu Lys Arg
       130                 135                 140

Val Gly Gly Thr Val Thr Thr Ala Asn His Phe Ala Ala Trp Lys Ala
145                 150                 155                 160

Leu Gly Leu Glu Met Gly Thr Tyr Asn Tyr Met Ile Val Ser Thr Glu
                165                 170                 175

Gly Tyr Glu Ser Ser Gly Ser Ser Thr Ile Thr Val Ser
                180                 185

<210> SEQ ID NO 12
<211> LENGTH: 189
<212> TYPE: PRT
<213> ORGANISM: Acremonium cellulolyticus

<400> SEQUENCE: 12

Ser Ile Thr Thr Ser Gln Thr Gly Thr Asn Asn Gly Tyr Tyr Tyr Ser
1               5                   10                  15

Phe Trp Thr Asn Gly Gly Gly Glu Val Thr Tyr Thr Asn Gly Pro Asn
                20                  25                  30
```

Gly Glu Tyr Ser Val Thr Trp Val Asn Cys Gly Asp Phe Thr Ser Gly
            35                  40                  45

Lys Gly Trp Asn Pro Ala Asn Ala Gln Thr Val Thr Tyr Ser Gly Glu
 50                  55                  60

Phe Asn Thr Ser Gly Asn Ala Tyr Leu Ala Val Tyr Gly Trp Thr Thr
 65                  70                  75                  80

Asp Pro Leu Val Glu Tyr Tyr Ile Leu Glu Ser Tyr Gly Thr Tyr Asn
                 85                  90                  95

Pro Ser Ser Gly Leu Thr Leu Leu Gly Gln Val Thr Ser Asp Gly Gly
                100                 105                 110

Thr Tyr Asp Ile Tyr Ser Thr Gln Arg Val Asp Gln Pro Ser Ile Glu
            115                 120                 125

Gly Thr Ser Thr Phe Asn Gln Tyr Trp Ser Val Arg Thr Glu Lys Arg
130                 135                 140

Val Gly Gly Thr Val Thr Thr Ala Asn His Phe Ala Ala Trp Lys Ala
145                 150                 155                 160

Leu Gly Leu Glu Met Gly Thr Tyr Asn Tyr Met Ile Val Ser Thr Glu
                165                 170                 175

Gly Tyr Glu Ser Ser Gly Ser Ser Thr Ile Thr Val Ser
            180                 185

<210> SEQ ID NO 13
<211> LENGTH: 189
<212> TYPE: PRT
<213> ORGANISM: Acremonium cellulolyticus

<400> SEQUENCE: 13

Ser Ile Thr Thr Ser Gln Thr Gly Thr Asn Asn Gly Tyr Tyr Tyr Ser
 1               5                  10                  15

Phe Trp Thr Asn Gly Gly Gly Glu Val Thr Tyr Thr Asn Gly Asp Gly
                 20                  25                  30

Gly Glu Tyr Ser Val Thr Trp Val Asn Cys Gly Asp Phe Thr Ser Gly
            35                  40                  45

Lys Gly Trp Asn Pro Ala Asn Ala Gln Thr Val Thr Tyr Ser Gly Glu
 50                  55                  60

Phe Asn Thr Ser Gly Asn Ala Tyr Leu Ala Val Tyr Gly Trp Thr Thr
 65                  70                  75                  80

Asp Pro Leu Val Glu Tyr Tyr Ile Leu Glu Ser Tyr Gly Thr Tyr Asn
                 85                  90                  95

Pro Ser Ser Gly Leu Thr Leu Leu Gly Gln Val Thr Ser Asp Gly Gly
                100                 105                 110

Thr Tyr Asp Ile Tyr Ser Thr Gln Arg Val Asp Gln Pro Ser Ile Glu
            115                 120                 125

Gly Thr Ser Thr Phe Asn Gln Tyr Trp Ser Val Arg Thr Glu Lys Arg
130                 135                 140

Val Gly Gly Thr Val Thr Thr Ala Asn His Phe Ala Ala Trp Lys Ala
145                 150                 155                 160

Leu Gly Leu Glu Met Gly Thr Tyr Asn Tyr Met Ile Val Ser Thr Glu
                165                 170                 175

Gly Tyr Glu Ser Ser Gly Ser Ser Thr Ile Thr Val Ser
            180                 185

<210> SEQ ID NO 14
<211> LENGTH: 27
<212> TYPE: DNA

```
<213> ORGANISM: Artificial
<220> FEATURE:
<223> OTHER INFORMATION: Forward primer for a mutation

<400> SEQUENCE: 14
gatatacata tgtgtatcac gacgagc                                      27

<210> SEQ ID NO 15
<211> LENGTH: 27
<212> TYPE: DNA
<213> ORGANISM: Artificial
<220> FEATURE:
<223> OTHER INFORMATION: Reverse primer for mutation

<400> SEQUENCE: 15
gctcgtcgtg atacacatat gtatatc                                      27

<210> SEQ ID NO 16
<211> LENGTH: 30
<212> TYPE: DNA
<213> ORGANISM: Artificial
<220> FEATURE:
<223> OTHER INFORMATION: Forward primer for a mutation

<400> SEQUENCE: 16
actgggacgc acaacggcta ctactactcg                                   30

<210> SEQ ID NO 17
<211> LENGTH: 29
<212> TYPE: DNA
<213> ORGANISM: Artificial
<220> FEATURE:
<223> OTHER INFORMATION: Reverse primer for a mutation

<400> SEQUENCE: 17
cgagtagtag tagccgttgt gcgtcccag                                    29

<210> SEQ ID NO 18
<211> LENGTH: 28
<212> TYPE: DNA
<213> ORGANISM: Artificial
<220> FEATURE:
<223> OTHER INFORMATION: Forward primer for a mutation

<400> SEQUENCE: 18
gtcacctact gtaatggtga caatggcg                                     28

<210> SEQ ID NO 19
<211> LENGTH: 30
<212> TYPE: DNA
<213> ORGANISM: Artificial
<220> FEATURE:
<223> OTHER INFORMATION: Reverse primer for a mutation

<400> SEQUENCE: 19
ttcgccattg tcaccattac agtaggtgac                                   30

<210> SEQ ID NO 20
<211> LENGTH: 30
<212> TYPE: DNA
<213> ORGANISM: Artificial
<220> FEATURE:
<223> OTHER INFORMATION: Forward primer for a mutation

<400> SEQUENCE: 20
acctacacat taggtgacaa tggcgaatac                                   30
```

<210> SEQ ID NO 21
<211> LENGTH: 29
<212> TYPE: DNA
<213> ORGANISM: Artificial
<220> FEATURE:
<223> OTHER INFORMATION: Reverse primer for a mutation

<400> SEQUENCE: 21
gtattcgcca ttgtcaccta atgtgtagg                              29

<210> SEQ ID NO 22
<211> LENGTH: 27
<212> TYPE: DNA
<213> ORGANISM: Artificial
<220> FEATURE:
<223> OTHER INFORMATION: Forward primer for a mutation

<400> SEQUENCE: 22
ggagaattta atcccagcgg aaacgct                                27

<210> SEQ ID NO 23
<211> LENGTH: 27
<212> TYPE: DNA
<213> ORGANISM: Artificial
<220> FEATURE:
<223> OTHER INFORMATION: Reverse primer for a mutation

<400> SEQUENCE: 23
agcgtttccg ctgggattaa attctcc                                27

<210> SEQ ID NO 24
<211> LENGTH: 27
<212> TYPE: DNA
<213> ORGANISM: Artificial
<220> FEATURE:
<223> OTHER INFORMATION: Forward primer for a mutation

<400> SEQUENCE: 24
gaatttaata caaacggaaa cgcttat                                27

<210> SEQ ID NO 25
<211> LENGTH: 27
<212> TYPE: DNA
<213> ORGANISM: Artificial
<220> FEATURE:
<223> OTHER INFORMATION: Reverse primer for a mutation

<400> SEQUENCE: 25
ataagcgttt ccgtttgtat taaattc                                27

<210> SEQ ID NO 26
<211> LENGTH: 30
<212> TYPE: DNA
<213> ORGANISM: Artificial
<220> FEATURE:
<223> OTHER INFORMATION: Forward primer for a mutation

<400> SEQUENCE: 26
gaagtcacca tgacaaatgg tgacaatggc                             30

<210> SEQ ID NO 27
<211> LENGTH: 30
<212> TYPE: DNA
<213> ORGANISM: Artificial
<220> FEATURE:

<223> OTHER INFORMATION: Reverse primer for a mutation

<400> SEQUENCE: 27
gccattgtca ccatttgtca tggtgacttc                                              30

<210> SEQ ID NO 28
<211> LENGTH: 29
<212> TYPE: DNA
<213> ORGANISM: Artificial
<220> FEATURE:
<223> OTHER INFORMATION: Forward primer for a mutation

<400> SEQUENCE: 28
cctacacaaa tggtcctaac ggcgaatac                                               29

<210> SEQ ID NO 29
<211> LENGTH: 29
<212> TYPE: DNA
<213> ORGANISM: Artificial
<220> FEATURE:
<223> OTHER INFORMATION: Reverse primer for a mutation

<400> SEQUENCE: 29
gtattcgccg ttaggaccat ttgtgtagg                                               29

<210> SEQ ID NO 30
<211> LENGTH: 27
<212> TYPE: DNA
<213> ORGANISM: Artificial
<220> FEATURE:
<223> OTHER INFORMATION: Forward primer for a mutation

<400> SEQUENCE: 30
acaaatggtg atggaggcga atacagc                                                 27

<210> SEQ ID NO 31
<211> LENGTH: 27
<212> TYPE: DNA
<213> ORGANISM: Artificial
<220> FEATURE:
<223> OTHER INFORMATION: Reverse primer for a mutation

<400> SEQUENCE: 31
gctgtattcg cctccatcac catttgt                                                 27

<210> SEQ ID NO 32
<211> LENGTH: 735
<212> TYPE: DNA
<213> ORGANISM: Acremonium cellulolyticus

<400> SEQUENCE: 32
atgaagctct ctctggctgc aattggcatt tgcacaactg ccgccgtcgc ctttccatct     60
ggacttactc aacacgctac gggagatctc agcaagcgtc aatcaatcac gacgagccag    120
actgggacga caacggcta ctactactcg ttctggacca acggcggagg agaagtcacc    180
tacacaaatg gtgacaatgg cgaatacagc gtgacctggg tcaattgcgg tgactttaca    240
tctggcaagg gctggaatcc agctaatgca cagtaagttt ctatttttgt tgtgttctaa    300
gcttatattt tacatactca catcggaatt tgaaggactg tcacctactc tggagaattt    360
aatacctctg gaaacgctta tctcgccgtt tacggttgga caactgatcc tcttgtcgaa    420
tactacatcc tggagtccta cggtacatat aacccatcat ctggccttac attacttggc    480
caggttacta gcgatggtgg tacgtacgat atctactcaa cacagcgtgt cgaccaaccc    540

```
tccatcgagg gaacttccac cttcaatcag tactggtcgg ttcgcacaga gaagcgagtc    600
ggcggaactg tcaccacggc caaccacttt gcagcatgga aggcacttgg acttgaaatg    660
ggtacttata actatatgat tgtgtctaca aaggctacg agagcagtgg ttctagtacc    720
atcaccgtgt cctag                                                      735
```

<210> SEQ ID NO 33
<211> LENGTH: 633
<212> TYPE: DNA
<213> ORGANISM: Acremonium cellulolyticus

<400> SEQUENCE: 33

```
tcaatcacga cgagccagac tgggacgaac aacggctact actactcgtt ctggaccaac     60
ggcggaggag aagtcaccta cacaaatggt gacaatggcg aatacagcgt gacctgggtc    120
aattgcggtg actttacatc tggcaagggc tggaatccag ctaatgcaca gtaagttttc    180
tattttgttg tgttctaagc ttatatttta catactcaca tcggaatttg aaggactgtc    240
acctactctg gagaatttaa tacctctgga aacgcttatc tcgccgttta cggttggaca    300
actgatcctc ttgtcgaata ctacatcctg gagtcctacg gtacatataa cccatcatct    360
ggccttacat tacttggcca ggttactagc gatggtggta cgtacgatat ctactcaaca    420
cagcgtgtcg accaaccctc catcgaggga acttccacct tcaatcagta ctggtcggtt    480
cgcacagaga agcgagtcgg cggaactgtc accacggcca accactttgc agcatggaag    540
gcacttggac ttgaaatggg tacttataac tatatgattg tgtctacaga aggctacgag    600
agcagtggtt ctagtaccat caccgtgtcc tag                                 633
```

<210> SEQ ID NO 34
<211> LENGTH: 633
<212> TYPE: DNA
<213> ORGANISM: Acremonium cellulolyticus

<400> SEQUENCE: 34

```
tgtatcacga cgagccagac tgggacgaac aacggctact actactcgtt ctggaccaac     60
ggcggaggag aagtcaccta cacaaatggt gacaatggcg aatacagcgt gacctgggtc    120
aattgcggtg actttacatc tggcaagggc tggaatccag ctaatgcaca gtaagttttc    180
tattttgttg tgttctaagc ttatatttta catactcaca tcggaatttg aaggactgtc    240
acctactctg gagaatttaa tacctctgga aacgcttatc tcgccgttta cggttggaca    300
actgatcctc ttgtcgaata ctacatcctg gagtcctacg gtacatataa cccatcatct    360
ggccttacat tacttggcca ggttactagc gatggtggta cgtacgatat ctactcaaca    420
cagcgtgtcg accaaccctc catcgaggga acttccacct tcaatcagta ctggtcggtt    480
cgcacagaga agcgagtcgg cggaactgtc accacggcca accactttgc agcatggaag    540
gcacttggac ttgaaatggg tacttataac tatatgattg tgtctacaga aggctacgag    600
agcagtggtt ctagtaccat caccgtgtcc tag                                 633
```

<210> SEQ ID NO 35
<211> LENGTH: 633
<212> TYPE: DNA
<213> ORGANISM: Acremonum cellulolyticus

<400> SEQUENCE: 35

```
tcaatcacga cgagccagac tgggacgcac aacggctact actactcgtt ctggaccaac     60
```

```
ggcggaggag aagtcaccta cacaaatggt gacaatggcg aatacagcgt gacctgggtc    120
aattgcggtg actttacatc tggcaagggc tggaatccag ctaatgcaca gtaagttttc    180
tattttgttg tgttctaagc ttatatttta catactcaca tcggaatttg aaggactgtc    240
acctactctg gagaatttaa tacctctgga aacgcttatc tcgccgttta cggttggaca    300
actgatcctc ttgtcgaata ctacatcctg gagtcctacg gtacatataa cccatcatct    360
ggccttacat tacttggcca ggttactagc gatggtggta cgtacgatat ctactcaaca    420
cagcgtgtcg accaaccctc catcgaggga acttccacct tcaatcagta ctggtcggtt    480
cgcacagaga agcgagtcgg cggaactgtc accacggcca accactttgc agcatggaag    540
gcacttggac ttgaaatggg tacttataac tatatgattg tgtctacaga aggctacgag    600
agcagtggtt ctagtaccat caccgtgtcc tag                                 633
```

```
<210> SEQ ID NO 36
<211> LENGTH: 633
<212> TYPE: DNA
<213> ORGANISM: Acremonium cellulolyticus

<400> SEQUENCE: 36
tcaatcacga cgagccagac tgggacgaac aacggctact actactcgtt ctggaccaac     60
ggcggaggag aagtcaccta ctgtaatggt gacaatggcg aatacagcgt gacctgggtc    120
aattgcggtg actttacatc tggcaagggc tggaatccag ctaatgcaca gtaagttttc    180
tattttgttg tgttctaagc ttatatttta catactcaca tcggaatttg aaggactgtc    240
acctactctg gagaatttaa tacctctgga aacgcttatc tcgccgttta cggttggaca    300
actgatcctc ttgtcgaata ctacatcctg gagtcctacg gtacatataa cccatcatct    360
ggccttacat tacttggcca ggttactagc gatggtggta cgtacgatat ctactcaaca    420
cagcgtgtcg accaaccctc catcgaggga acttccacct tcaatcagta ctggtcggtt    480
cgcacagaga agcgagtcgg cggaactgtc accacggcca accactttgc agcatggaag    540
gcacttggac ttgaaatggg tacttataac tatatgattg tgtctacaga aggctacgag    600
agcagtggtt ctagtaccat caccgtgtcc tag                                 633
```

```
<210> SEQ ID NO 37
<211> LENGTH: 633
<212> TYPE: DNA
<213> ORGANISM: Acremonium cellulolyticus

<400> SEQUENCE: 37
tcaatcacga cgagccagac tgggacgaac aacggctact actactcgtt ctggaccaac     60
ggcggaggag aagtcaccta cacattaggt gacaatggcg aatacagcgt gacctgggtc    120
aattgcggtg actttacatc tggcaagggc tggaatccag ctaatgcaca gtaagttttc    180
tattttgttg tgttctaagc ttatatttta catactcaca tcggaatttg aaggactgtc    240
acctactctg gagaatttaa tacctctgga aacgcttatc tcgccgttta cggttggaca    300
actgatcctc ttgtcgaata ctacatcctg gagtcctacg gtacatataa cccatcatct    360
ggccttacat tacttggcca ggttactagc gatggtggta cgtacgatat ctactcaaca    420
cagcgtgtcg accaaccctc catcgaggga acttccacct tcaatcagta ctggtcggtt    480
cgcacagaga agcgagtcgg cggaactgtc accacggcca accactttgc agcatggaag    540
gcacttggac ttgaaatggg tacttataac tatatgattg tgtctacaga aggctacgag    600
agcagtggtt ctagtaccat caccgtgtcc tag                                 633
```

<210> SEQ ID NO 38
<211> LENGTH: 633
<212> TYPE: DNA
<213> ORGANISM: Acremonium cellulolyticus

<400> SEQUENCE: 38

| | | | | | |
|---|---|---|---|---|---|
| tcaatcacga | cgagccagac | tgggacgaac | aacggctact | actactcgtt | ctggaccaac | 60 |
| ggcggaggag | aagtcaccta | cacaaatggt | gacaatggcg | aatacagcgt | gacctgggtc | 120 |
| aattgcggtg | actttacatc | tggcaagggc | tggaatccag | ctaatgcaca | gtaagttttc | 180 |
| tattttgttg | tgttctaagc | ttatatttta | catactcaca | tcggaatttg | aaggactgtc | 240 |
| acctactctg | gagaatttaa | tcccagcgga | aacgcttatc | tcgccgttta | cggttggaca | 300 |
| actgatcctc | ttgtcgaata | ctacatcctg | gagtcctacg | gtacatataa | cccatcatct | 360 |
| ggccttacat | tacttggcca | ggttactagc | gatggtggta | cgtacgatat | ctactcaaca | 420 |
| cagcgtgtcg | accaaccctc | catcgaggga | acttccacct | tcaatcagta | ctggtcggtt | 480 |
| cgcacagaga | agcgagtcgg | cggaactgtc | accacggcca | accactttgc | agcatggaag | 540 |
| gcacttggac | ttgaaatggg | tacttataac | tatatgattg | tgtctacaga | aggctacgag | 600 |
| agcagtggtt | ctagtaccat | caccgtgtcc | tag | | | 633 |

<210> SEQ ID NO 39
<211> LENGTH: 633
<212> TYPE: DNA
<213> ORGANISM: Acremonium cellulolyticus

<400> SEQUENCE: 39

| | | | | | |
|---|---|---|---|---|---|
| tcaatcacga | cgagccagac | tgggacgaac | aacggctact | actactcgtt | ctggaccaac | 60 |
| ggcggaggag | aagtcaccta | cacaaatggt | gacaatggcg | aatacagcgt | gacctgggtc | 120 |
| aattgcggtg | actttacatc | tggcaagggc | tggaatccag | ctaatgcaca | gtaagttttc | 180 |
| tattttgttg | tgttctaagc | ttatatttta | catactcaca | tcggaatttg | aaggactgtc | 240 |
| acctactctg | gagaatttaa | tacaaacgga | aacgcttatc | tcgccgttta | cggttggaca | 300 |
| actgatcctc | ttgtcgaata | ctacatcctg | gagtcctacg | gtacatataa | cccatcatct | 360 |
| ggccttacat | tacttggcca | ggttactagc | gatggtggta | cgtacgatat | ctactcaaca | 420 |
| cagcgtgtcg | accaaccctc | catcgaggga | acttccacct | tcaatcagta | ctggtcggtt | 480 |
| cgcacagaga | agcgagtcgg | cggaactgtc | accacggcca | accactttgc | agcatggaag | 540 |
| gcacttggac | ttgaaatggg | tacttataac | tatatgattg | tgtctacaga | aggctacgag | 600 |
| agcagtggtt | ctagtaccat | caccgtgtcc | tag | | | 633 |

<210> SEQ ID NO 40
<211> LENGTH: 633
<212> TYPE: DNA
<213> ORGANISM: Acremonium cellulolyticus

<400> SEQUENCE: 40

| | | | | | |
|---|---|---|---|---|---|
| tgtatcacga | cgagccagac | tgggacgaac | aacggctact | actactcgtt | ctggaccaac | 60 |
| ggcggaggag | aagtcaccta | ctgtaatggt | gacaatggcg | aatacagcgt | gacctgggtc | 120 |
| aattgcggtg | actttacatc | tggcaagggc | tggaatccag | ctaatgcaca | gtaagttttc | 180 |
| tattttgttg | tgttctaagc | ttatatttta | catactcaca | tcggaatttg | aaggactgtc | 240 |
| acctactctg | gagaatttaa | tacctctgga | aacgcttatc | tcgccgttta | cggttggaca | 300 |

| | |
|---|---|
| actgatcctc ttgtcgaata ctacatcctg gagtcctacg gtacatataa cccatcatct | 360 |
| ggccttacat tacttggcca ggttactagc gatggtggta cgtacgatat ctactcaaca | 420 |
| cagcgtgtcg accaaccctc catcgaggga acttccacct tcaatcagta ctggtcggtt | 480 |
| cgcacagaga agcgagtcgg cggaactgtc accacggcca accactttgc agcatggaag | 540 |
| gcacttggac ttgaaatggg tacttataac tatatgattg tgtctacaga aggctacgag | 600 |
| agcagtggtt ctagtaccat caccgtgtcc tag | 633 |

<210> SEQ ID NO 41
<211> LENGTH: 633
<212> TYPE: DNA
<213> ORGANISM: Acremonium cellulolyticus

<400> SEQUENCE: 41

| | |
|---|---|
| tgtatcacga cgagccagac tgggacgcac aacggctact actactcgtt ctggaccaac | 60 |
| ggcggaggag aagtcaccat gtgtttaggt cctggaggcg aatacagcgt gacctgggtc | 120 |
| aattgcggtg actttacatc tggcaagggc tggaatccag ctaatgcaca gtaagttttc | 180 |
| tattttgttg tgttctaagc ttatatttta catactcaca tcggaatttg aaggactgtc | 240 |
| acctactctg gagaatttaa tcccaacgga aacgcttatc tcgccgttta cggttggaca | 300 |
| actgatcctc ttgtcgaata ctacatcctg gagtcctacg gtacatataa cccatcatct | 360 |
| ggccttacat tacttggcca ggttactagc gatggtggta cgtacgatat ctactcaaca | 420 |
| cagcgtgtcg accaaccctc catcgaggga acttccacct tcaatcagta ctggtcggtt | 480 |
| cgcacagaga agcgagtcgg cggaactgtc accacggcca accactttgc agcatggaag | 540 |
| gcacttggac ttgaaatggg tacttataac tatatgattg tgtctacaga aggctacgag | 600 |
| agcagtggtt ctagtaccat caccgtgtcc tag | 633 |

<210> SEQ ID NO 42
<211> LENGTH: 633
<212> TYPE: DNA
<213> ORGANISM: Acremonium cellulolyticus

<400> SEQUENCE: 42

| | |
|---|---|
| tcaatcacga cgagccagac tgggacgaac aacggctact actactcgtt ctggaccaac | 60 |
| ggcggaggag aagtcaccat gacaaatggt gacaatggcg aatacagcgt gacctgggtc | 120 |
| aattgcggtg actttacatc tggcaagggc tggaatccag ctaatgcaca gtaagttttc | 180 |
| tattttgttg tgttctaagc ttatatttta catactcaca tcggaatttg aaggactgtc | 240 |
| acctactctg gagaatttaa tcctctgga aacgcttatc tcgccgttta cggttggaca | 300 |
| actgatcctc ttgtcgaata ctacatcctg gagtcctacg gtacatataa cccatcatct | 360 |
| ggccttacat tacttggcca ggttactagc gatggtggta cgtacgatat ctactcaaca | 420 |
| cagcgtgtcg accaaccctc catcgaggga acttccacct tcaatcagta ctggtcggtt | 480 |
| cgcacagaga agcgagtcgg cggaactgtc accacggcca accactttgc agcatggaag | 540 |
| gcacttggac ttgaaatggg tacttataac tatatgattg tgtctacaga aggctacgag | 600 |
| agcagtggtt ctagtaccat caccgtgtcc tag | 633 |

<210> SEQ ID NO 43
<211> LENGTH: 633
<212> TYPE: DNA
<213> ORGANISM: Acremonium cellulolyticus

<400> SEQUENCE: 43

```
tcaatcacga cgagccagac tgggacgaac aacggctact actactcgtt ctggaccaac      60
ggcggaggag aagtcaccta cacaaatggt cctaatggcg aatacagcgt gacctgggtc     120
aattgcggtg actttacatc tggcaagggc tggaatccag ctaatgcaca gtaagttttc     180
tattttgttg tgttctaagc ttatatttta catactcaca tcggaatttg aaggactgtc     240
acctactctg gagaatttaa tacctctgga aacgcttatc tcgccgttta cggttggaca     300
actgatcctc ttgtcgaata ctacatcctg gagtcctacg gtacatataa cccatcatct     360
ggccttacat tacttggcca ggttactagc gatggtggta cgtacgatat ctactcaaca     420
cagcgtgtcg accaaccctc catcgaggga acttccacct tcaatcagta ctggtcggtt     480
cgcacagaga agcgagtcgg cggaactgtc accacggcca accactttgc agcatggaag     540
gcacttggac ttgaaatggg tacttataac tatatgattg tgtctacaga aggctacgag     600
agcagtggtt ctagtaccat caccgtgtcc tag                                  633
```

```
<210> SEQ ID NO 44
<211> LENGTH: 633
<212> TYPE: DNA
<213> ORGANISM: Acremonium cellulolyticus

<400> SEQUENCE: 44
```

```
tcaatcacga cgagccagac tgggacgaac aacggctact actactcgtt ctggaccaac      60
ggcggaggag aagtcaccta cacaaatggt gatggaggcg aatacagcgt gacctgggtc     120
aattgcggtg actttacatc tggcaagggc tggaatccag ctaatgcaca gtaagttttc     180
tattttgttg tgttctaagc ttatatttta catactcaca tcggaatttg aaggactgtc     240
acctactctg gagaatttaa tacctctgga aacgcttatc tcgccgttta cggttggaca     300
actgatcctc ttgtcgaata ctacatcctg gagtcctacg gtacatataa cccatcatct     360
ggccttacat tacttggcca ggttactagc gatggtggta cgtacgatat ctactcaaca     420
cagcgtgtcg accaaccctc catcgaggga acttccacct tcaatcagta ctggtcggtt     480
cgcacagaga agcgagtcgg cggaactgtc accacggcca accactttgc agcatggaag     540
gcacttggac ttgaaatggg tacttataac tatatgattg tgtctacaga aggctacgag     600
agcagtggtt ctagtaccat caccgtgtcc tag                                  633
```

```
<210> SEQ ID NO 45
<211> LENGTH: 189
<212> TYPE: PRT
<213> ORGANISM: Acremonium cellulolyticus

<400> SEQUENCE: 45
```

```
Cys Ile Thr Thr Ser Gln Thr Gly Thr His Asn Gly Tyr Tyr Tyr Ser
1               5                   10                  15

Phe Trp Thr Asn Gly Gly Gly Glu Val Thr Met Cys Leu Gly Pro Gly
                20                  25                  30

Gly Glu Tyr Ser Val Thr Trp Val Asn Cys Gly Asp Phe Thr Ser Gly
            35                  40                  45

Lys Gly Trp Asn Pro Ala Asn Ala Gln Thr Val Thr Tyr Ser Gly Glu
        50                  55                  60

Phe Asn Thr Ser Gly Asn Ala Tyr Leu Ala Val Tyr Gly Trp Thr Thr
65                  70                  75                  80

Asp Pro Leu Val Glu Tyr Tyr Ile Leu Glu Ser Tyr Gly Thr Tyr Asn
                85                  90                  95
```

```
Pro Ser Ser Gly Leu Thr Leu Leu Gly Gln Val Thr Ser Asp Gly
            100                 105                 110
Thr Tyr Asp Ile Tyr Ser Thr Gln Arg Val Asp Gln Pro Ser Ile Glu
        115                 120                 125
Gly Thr Ser Thr Phe Asn Gln Tyr Trp Ser Val Arg Thr Glu Lys Arg
        130                 135                 140
Val Gly Gly Thr Val Thr Thr Ala Asn His Phe Ala Ala Trp Lys Ala
145                 150                 155                 160
Leu Gly Leu Glu Met Gly Thr Tyr Asn Tyr Met Ile Val Ser Thr Glu
                165                 170                 175
Gly Tyr Glu Ser Ser Gly Ser Ser Thr Ile Thr Val Ser
        180                 185

<210> SEQ ID NO 46
<211> LENGTH: 89
<212> TYPE: PRT
<213> ORGANISM: Saccharomyces cerevisiae

<400> SEQUENCE: 46

Met Arg Phe Pro Ser Ile Phe Thr Ala Val Leu Phe Ala Ala Ser Ser
1               5                   10                  15
Ala Leu Ala Ala Pro Val Asn Thr Thr Thr Glu Asp Glu Thr Ala Gln
                20                  25                  30
Ile Pro Ala Glu Ala Val Ile Gly Tyr Ser Asp Leu Glu Gly Asp Phe
            35                  40                  45
Asp Val Ala Val Leu Pro Phe Ser Asn Ser Thr Asn Asn Gly Leu Leu
        50                  55                  60
Phe Ile Asn Thr Thr Ile Ala Ser Ile Ala Ala Lys Glu Glu Gly Val
65                  70                  75                  80
Ser Leu Glu Lys Arg Glu Ala Glu Ala
                85

<210> SEQ ID NO 47
<211> LENGTH: 570
<212> TYPE: DNA
<213> ORGANISM: Acremonium cellulolyticus

<400> SEQUENCE: 47
tcaatcacga cgagccagac tgggacgaac aacggctact actactcgtt ctggaccaac      60
ggcggaggag aagtcaccta cacaaatggt gacaatggcg aatacagcgt gacctgggtc     120
aattgcggtg actttacatc tggcaagggc tggaatccag ctaatgccca gactgtcacc     180
tactctggag aatttaatac ctctggaaac gcttatctcg ccgtttacgg ttggacaact     240
gatcctcttg tcgaatacta catcctggag tcctacggta catataaccc atcatctggc     300
cttacattac ttggccaggt tactagcgat ggtggtacgt acgatatcta ctcaacacag     360
cgtgtcgacc aaccctccat cgagggaact tccaccttca atcagtactg gtcggttcgc     420
acagagaagc gagtcggcgg aactgtcacc acggccaacc actttgcagc atggaaggca     480
cttggacttg aaatgggtac ttataactat atgattgtgt ctacagaagg ctacgagagc     540
agtggttcta gtaccatcac cgtgtcctag                                     570

<210> SEQ ID NO 48
<211> LENGTH: 570
<212> TYPE: DNA
<213> ORGANISM: Acremonium cellulolyticus

<400> SEQUENCE: 48
```

```
tgtatcacga cgagccagac tgggacgaac aacggctact actactcgtt ctggaccaac      60
ggcggaggag aagtcaccta ctgtaatggt gacaatggcg aatacagcgt gacctgggtc     120
aattgcggtg actttacatc tggcaagggc tggaatccag ctaatgccca gactgtcacc     180
tactctggag aatttaatac ctctggaaac gcttatctcg ccgtttacgg ttggacaact     240
gatcctcttg tcgaatacta catcctggag tcctacggta catataaccc atcatctggc     300
cttacattac ttggccaggt tactagcgat ggtggtacgt acgatatcta ctcaacacag     360
cgtgtcgacc aaccctccat cgagggaact tccaccttca atcagtactg gtcggttcgc     420
acagagaagc gagtcggcgg aactgtcacc acggccaacc actttgcagc atggaaggca     480
cttggacttg aaatgggtac ttataactat atgattgtgt ctacagaagg ctacgagagc     540
agtggttcta gtaccatcac cgtgtcctag                                      570
```

<210> SEQ ID NO 49
<211> LENGTH: 570
<212> TYPE: DNA
<213> ORGANISM: Acremonium cellulolyticus

<400> SEQUENCE: 49

```
tgtatcacga cgagccagac tgggacgcac aacggctact actactcgtt ctggaccaac      60
ggcggaggag aagtcaccat gtgtttaggt cctggtggcg aatacagcgt gacctgggtc     120
aattgcggtg actttacatc tggcaagggc tggaatccag ctaatgccca gactgtcacc     180
tactctggag aatttaatac ctctggaaac gcttatctcg ccgtttacgg ttggacaact     240
gatcctcttg tcgaatacta catcctggag tcctacggta catataaccc atcatctggc     300
cttacattac ttggccaggt tactagcgat ggtggtacgt acgatatcta ctcaacacag     360
cgtgtcgacc aaccctccat cgagggaact tccaccttca atcagtactg gtcggttcgc     420
acagagaagc gagtcggcgg aactgtcacc acggccaacc actttgcagc atggaaggca     480
cttggacttg aaatgggtac ttataactat atgattgtgt ctacagaagg ctacgagagc     540
agtggttcta gtaccatcac cgtgtcctag                                      570
```

<210> SEQ ID NO 50
<211> LENGTH: 570
<212> TYPE: DNA
<213> ORGANISM: Acremonium cellulolyticus

<400> SEQUENCE: 50

```
tgtatcacga cgagccagac tgggacgcac aacggctact actactcgtt ctggaccaac      60
ggcggaggag aagtcaccat gtgtttaggt cctggtggcg aatacagcgt gacctgggtc     120
aattgcggtg actttacatc tggcaagggc tggaatccag ctaatgccca gactgtcacc     180
tactctggag aatttaatcc caatggaaac gcttatctcg ccgtttacgg ttggacaact     240
gatcctcttg tcgaatacta catcctggag tcctacggta catataaccc atcatctggc     300
cttacattac ttggccaggt tactagcgat ggtggtacgt acgatatcta ctcaacacag     360
cgtgtcgacc aaccctccat cgagggaact tccaccttca atcagtactg gtcggttcgc     420
acagagaagc gagtcggcgg aactgtcacc acggccaacc actttgcagc atggaaggca     480
cttggacttg aaatgggtac ttataactat atgattgtgt ctacagaagg ctacgagagc     540
agtggttcta gtaccatcac cgtgtcctag                                      570
```

<210> SEQ ID NO 51

```
<211> LENGTH: 52
<212> TYPE: DNA
<213> ORGANISM: Artificial
<220> FEATURE:
<223> OTHER INFORMATION: Forward primer for a transformation

<400> SEQUENCE: 51
tacacgtact tagtcgctga agctcttcta tgtcaatcac gacgagccag ac         52

<210> SEQ ID NO 52
<211> LENGTH: 52
<212> TYPE: DNA
<213> ORGANISM: Artificial
<220> FEATURE:
<223> OTHER INFORMATION: Forward primer for a transformation

<400> SEQUENCE: 52
tacacgtact tagtcgctga agctcttcta tgtgtatcac gacgagccag ac         52

<210> SEQ ID NO 53
<211> LENGTH: 54
<212> TYPE: DNA
<213> ORGANISM: Artificial
<220> FEATURE:
<223> OTHER INFORMATION: Reverse primer for a transformation

<400> SEQUENCE: 53
taggtacgaa ctcgattgac ggctcttcta ccctaggaca cggtgatggt acta       54

<210> SEQ ID NO 54
<211> LENGTH: 32
<212> TYPE: DNA
<213> ORGANISM: Artificial
<220> FEATURE:
<223> OTHER INFORMATION: Restriction site for a transformation

<400> SEQUENCE: 54
tacacgtact tagtcgctga agctcttcta tg                               32

<210> SEQ ID NO 55
<211> LENGTH: 31
<212> TYPE: DNA
<213> ORGANISM: Artificial
<220> FEATURE:
<223> OTHER INFORMATION: Restriction site for a transformation

<400> SEQUENCE: 55
ggtagaagag ccgtcaatcg agttcgtacc t                                31

<210> SEQ ID NO 56
<211> LENGTH: 267
<212> TYPE: DNA
<213> ORGANISM: Saccharomyces cerevisiae

<400> SEQUENCE: 56
atgagattcc catctatttt caccgctgtc ttgttcgctg cctcctctgc attggctgcc  60
cctgttaaca ctaccactga agacgagact gctcaaattc cagctgaagc agttatcggt 120
tactctgacc ttgagggtga tttcgacgtc gctgttttgc ctttctctaa ctccactaac 180
aacggtttgt tgttcattaa caccactatc gcttccattg ctgctaagga gagggtgtc  240 tctctcgaga aaagagaggc cgaagct                                    267
```